(12) United States Patent
Breingan

(10) Patent No.: US 12,734,289 B2
(45) Date of Patent: Sep. 15, 2026

(54) DRUG DELIVERY DEVICE DRIVE SENSOR

(71) Applicant: INSULET CORPORATION, Acton, MA (US)

(72) Inventor: Kyle Breingan, Lowell, MA (US)

(73) Assignee: INSULET CORPORATION, Acton, MA (US)

( * ) Notice: Subject to any disclaimer, the term of this patent is extended or adjusted under 35 U.S.C. 154(b) by 422 days.

(21) Appl. No.: 18/543,617

(22) Filed: Dec. 18, 2023

(65) Prior Publication Data

US 2024/0197983 A1 Jun. 20, 2024

Related U.S. Application Data

(60) Provisional application No. 63/476,076, filed on Dec. 19, 2022.

(51) Int. Cl.
*A61M 5/142* (2006.01)
*A61M 5/172* (2006.01)

(52) U.S. Cl.
CPC ........ *A61M 5/14216* (2013.01); *A61M 5/172* (2013.01)

(58) Field of Classification Search
CPC .......... A61M 5/14216; A61M 5/14244; A61M 5/172; A61M 2005/14506; A61M 2205/8212; F16D 41/18; F16H 31/005
See application file for complete search history.

(56) References Cited

U.S. PATENT DOCUMENTS 1,441,508 A 1/1923 Jensen
2,198,666 A 4/1940 Gruskin
2,752,918 A 7/1956 Uytenbogaar
3,176,712 A 4/1965 Ramsden
3,297,260 A 1/1967 Barlow
3,464,359 A 9/1969 King
3,885,662 A 5/1975 Schaefer
3,946,732 A 3/1976 Hurscham
3,947,692 A 3/1976 Payne
3,993,061 A 11/1976 OLeary
(Continued)

FOREIGN PATENT DOCUMENTS

CA 606281 A 10/1960
CN 1375338 A 10/2002
(Continued)

OTHER PUBLICATIONS

International Search Report and Written Opinion for PCT/US2018/014351, mailed on Jun. 4, 2018, 9 pages.
(Continued)

*Primary Examiner* — Cris L. Rodriguez
(74) *Attorney, Agent, or Firm* — Goodwin Procter LLP

(57) ABSTRACT

Disclosed are techniques for managing the application of a force by a drive mechanism in a drug delivery device as well as devices for implementing the disclosed techniques. One or more driving arms may be operable to drive a respective ratchet wheel and one or more sensor contacts may be positioned to determine when a respective driving arm is to be controlled to no longer drive the respective ratchet wheel thereby saving electrical power. The disclosed techniques and devices may be incorporated in a drug delivery device, such as those carried by a person or affixed to the skin of a person.

18 Claims, 12 Drawing Sheets

(56) References Cited

U.S. PATENT DOCUMENTS 4,108,177 A 8/1978 Pistor
4,152,098 A 5/1979 Moody et al.
4,210,173 A 7/1980 Choksi et al.
4,221,219 A 9/1980 Tucker
4,257,324 A 3/1981 Stefansson et al.
4,268,150 A 5/1981 Chen
4,277,226 A 7/1981 Archibald
4,313,439 A 2/1982 Babb et al.
4,371,790 A 2/1983 Manning et al.
4,417,889 A 11/1983 Choi
4,424,720 A 1/1984 Bucchianeri
4,435,173 A 3/1984 Siposs et al.
4,475,905 A 10/1984 Himmelstrup
4,498,843 A 2/1985 Schneider et al.
4,507,115 A 3/1985 Kambara et al.
4,551,134 A 11/1985 Slavik et al.
4,562,751 A 1/1986 Nason et al.
4,567,549 A 1/1986 Lemme
4,585,439 A 4/1986 Michel
4,601,707 A 7/1986 Albisser et al.
4,634,427 A 1/1987 Hannula et al.
4,671,429 A 6/1987 Spaanderman et al.
4,678,408 A 7/1987 Nason et al.
4,684,368 A 8/1987 Kenyon
4,685,903 A 8/1987 Cable et al.
4,755,169 A 7/1988 Sarnoff et al.
4,766,889 A 8/1988 Trick et al.
4,808,161 A 2/1989 Kamen
4,846,797 A 7/1989 Howson et al.
4,858,619 A 8/1989 Toth
4,898,579 A 2/1990 Groshong et al.
4,908,017 A 3/1990 Howson et al.
4,944,659 A 7/1990 Labbe et al.
4,969,874 A 11/1990 Michel et al.
4,991,743 A 2/1991 Walker
5,007,458 A 4/1991 Marcus et al.
5,020,325 A 6/1991 Henault
5,062,841 A 11/1991 Siegel
5,147,311 A 9/1992 Pickhard
5,178,609 A 1/1993 Ishikawa
5,205,819 A 4/1993 Ross et al.
5,213,483 A 5/1993 Flaherty et al.
5,222,362 A 6/1993 Maus et al.
5,236,416 A 8/1993 McDaniel et al.
5,261,882 A 11/1993 Sealfon
5,261,884 A 11/1993 Stern et al.
5,277,338 A 1/1994 Divall et al.
5,281,202 A 1/1994 Weber et al.
5,346,476 A 9/1994 Elson
5,364,342 A 11/1994 Beuchat et al.
5,388,615 A 2/1995 Edlund et al.
5,433,710 A 7/1995 VanAntwerp et al.
5,503,628 A 4/1996 Fetters et al.
5,520,661 A 5/1996 Lal et al.
5,533,389 A 7/1996 Kamen et al.
5,582,593 A 12/1996 Hultman
5,618,269 A 4/1997 Jacobsen et al.
5,628,309 A 5/1997 Brown
5,637,095 A 6/1997 Nason et al.
5,665,070 A 9/1997 McPhee
5,713,875 A 2/1998 Tanner, II
5,747,350 A 5/1998 Sattler
5,748,827 A 5/1998 Holl et al.
5,776,103 A 7/1998 Kriesel et al.
5,779,676 A 7/1998 Kriesel et al.
5,785,688 A 7/1998 Joshi et al.
5,797,881 A 8/1998 Gadot
5,800,397 A 9/1998 Wilson et al.
5,807,075 A 9/1998 Jacobsen et al.
5,839,467 A 11/1998 Saaski et al.
5,891,097 A 4/1999 Saito et al.
5,897,530 A 4/1999 Jackson
5,906,597 A 5/1999 McPhee
5,911,716 A 6/1999 Rake et al.
5,919,167 A 7/1999 Mulhauser et al.
5,957,890 A 9/1999 Mann et al.
5,961,492 A 10/1999 Kriesel et al.
5,971,963 A 10/1999 Choi
6,019,747 A 2/2000 McPhee
6,050,457 A 4/2000 Arnold et al.
6,068,615 A 5/2000 Brown et al.
6,159,188 A 12/2000 Laibovitz et al.
6,174,300 B1 1/2001 Kriesel et al.
6,190,359 B1 2/2001 Heruth
6,200,293 B1 3/2001 Kriesel et al.
6,352,522 B1 3/2002 Kim et al.
6,363,609 B1 4/2002 Pickren
6,375,638 B2 4/2002 Nason et al.
6,474,219 B2 11/2002 Klitmose et al.
6,485,461 B1 11/2002 Mason et al.
6,485,462 B1 11/2002 Kriesel
6,488,652 B1 12/2002 Weijand et al.
6,520,936 B1 2/2003 Mann
6,527,744 B1 3/2003 Kriesel et al.
6,537,249 B2 3/2003 Kriesell et al.
6,539,286 B1 3/2003 Jiang
6,569,115 B1 5/2003 Barker et al.
6,595,956 B1 7/2003 Gross et al.
6,656,158 B2 * 12/2003 Mahoney ............ A61M 5/1452 604/151
6,699,218 B2 3/2004 Flaherty et al.
6,723,072 B2 4/2004 Flaherty et al.
6,740,059 B2 5/2004 Flaherty
6,749,407 B2 6/2004 Xie et al.
6,851,260 B2 2/2005 Mernoe
6,883,778 B1 4/2005 Newton et al.
7,018,360 B2 3/2006 Flaherty et al.
7,104,275 B2 9/2006 Dille
7,128,727 B2 10/2006 Flaherty et al.
7,137,964 B2 11/2006 Flaherty
7,144,384 B2 * 12/2006 Gorman ............. A61M 5/1452 604/151
7,160,272 B1 1/2007 Eyal et al.
7,303,549 B2 12/2007 Flaherty
7,771,392 B2 8/2010 De Polo et al.
7,914,499 B2 3/2011 Gonnelli et al.
7,951,114 B2 5/2011 Rush et al.
8,267,921 B2 9/2012 Yodfat et al.
8,382,703 B1 2/2013 Abdelaal
8,499,913 B2 8/2013 Gunter
8,597,244 B2 12/2013 Mernoe
8,905,995 B2 12/2014 Mernoe
8,920,376 B2 12/2014 Caffey et al.
8,939,935 B2 1/2015 OConnor et al.
9,180,244 B2 11/2015 Anderson et al.
9,192,716 B2 11/2015 Jugl et al.
9,402,950 B2 8/2016 Dilanni et al.
9,539,596 B2 1/2017 Ikushima
10,441,723 B2 10/2019 Nazzaro
10,695,485 B2 6/2020 Nazzaro
10,780,217 B2 * 9/2020 Nazzaro ............ A61M 5/16804
2001/0016710 A1 8/2001 Nason et al.
2001/0056258 A1 12/2001 Evans
2002/0029018 A1 3/2002 Jeffrey
2002/0032374 A1 3/2002 Holker et al.
2002/0037221 A1 3/2002 Mastrangelo et al.
2002/0173769 A1 11/2002 Gray et al.
2002/0173830 A1 11/2002 Starkweather et al.
2003/0040715 A1 2/2003 DAntonio et al.
2003/0055380 A1 3/2003 Flaherty
2003/0097092 A1 5/2003 Flaherty
2003/0109827 A1 6/2003 Lavi et al.
2003/0163097 A1 8/2003 Fleury et al.
2003/0198558 A1 10/2003 Nason et al.
2003/0199825 A1 10/2003 Flaherty
2004/0010207 A1 1/2004 Flaherty et al.
2004/0064088 A1 4/2004 Gorman et al.
2004/0068224 A1 4/2004 Couvillon, Jr. et al.
2004/0069044 A1 4/2004 Lavi et al.
2004/0092865 A1 5/2004 Flaherty et al.
2004/0094733 A1 5/2004 Hower et al.
2004/0153032 A1 8/2004 Garribotto et al.
2005/0020980 A1 1/2005 Inoue et al.
2005/0165363 A1 7/2005 Judson et al.

(56) References Cited

U.S. PATENT DOCUMENTS

| | | | |
|---|---|---|---|
| 2005/0203461 | A1 | 9/2005 | Flaherty et al. |
| 2005/0238507 | A1 | 10/2005 | Dilanni et al. |
| 2005/0273059 | A1 | 12/2005 | Mernoe |
| 2005/0277882 | A1 | 12/2005 | Kriesel |
| 2006/0041229 | A1 | 2/2006 | Garibotto et al. |
| 2006/0079765 | A1 | 4/2006 | Neer et al. |
| 2006/0155210 | A1 | 7/2006 | Beckman et al. |
| 2006/0173439 | A1 | 8/2006 | Thorne et al. |
| 2006/0178633 | A1 | 8/2006 | Garibotto et al. |
| 2006/0253085 | A1 | 11/2006 | Geismar et al. |
| 2006/0282290 | A1 | 12/2006 | Flaherty et al. |
| 2007/0005018 | A1 | 1/2007 | Tekbuchava |
| 2007/0073236 | A1 | 3/2007 | Merno et al. |
| 2007/0088271 | A1 | 4/2007 | Richards |
| 2007/0118405 | A1 | 5/2007 | Campbell et al. |
| 2007/0282269 | A1 | 12/2007 | Carter et al. |
| 2008/0004515 | A1 | 1/2008 | Jennewine |
| 2008/0051738 | A1 | 2/2008 | Griffin |
| 2008/0114304 | A1 | 5/2008 | Nalesso et al. |
| 2008/0172028 | A1 | 7/2008 | Blomquist |
| 2008/0243211 | A1 | 10/2008 | Cartwright et al. |
| 2008/0294040 | A1 | 11/2008 | Mohiuddin et al. |
| 2009/0024083 | A1 | 1/2009 | Kriesel et al. |
| 2009/0062767 | A1 | 3/2009 | Van Antwerp et al. |
| 2009/0198215 | A1 | 8/2009 | Chong et al. |
| 2009/0278875 | A1 | 11/2009 | Holm et al. |
| 2009/0326472 | A1 | 12/2009 | Carter et al. |
| 2010/0036326 | A1 | 2/2010 | Matusch |
| 2010/0152658 | A1 | 6/2010 | Hanson et al. |
| 2010/0241066 | A1 | 9/2010 | Hansen et al. |
| 2011/0054399 | A1 | 3/2011 | Chong et al. |
| 2011/0073620 | A1 | 3/2011 | Verrilli |
| 2011/0144586 | A1 | 6/2011 | Michaud et al. |
| 2011/0180480 | A1 | 7/2011 | Kloeffel et al. |
| 2011/0230833 | A1 | 9/2011 | Landman et al. |
| 2012/0078161 | A1 | 3/2012 | Masterson et al. |
| 2012/0172817 | A1 | 7/2012 | Bruggemann et al. |
| 2012/0209207 | A1 | 8/2012 | Gray et al. |
| 2013/0006213 | A1 | 1/2013 | Arnitz et al. |
| 2013/0017099 | A1 | 1/2013 | Genoud |
| 2013/0064701 | A1 | 3/2013 | Konishi |
| 2013/0177455 | A1 | 7/2013 | Kamen et al. |
| 2013/0178803 | A1 | 7/2013 | Raab |
| 2013/0245545 | A1 | 9/2013 | Arnold et al. |
| 2013/0267932 | A1 | 10/2013 | Franke et al. |
| 2013/0296792 | A1 | 11/2013 | Cabiri |
| 2014/0018730 | A1 | 1/2014 | Muller-Pathle |
| 2014/0127048 | A1 | 5/2014 | Dilanni et al. |
| 2014/0128839 | A1 | 5/2014 | Dilanni et al. |
| 2014/0142508 | A1 | 5/2014 | Dilanni et al. |
| 2014/0148784 | A1 | 5/2014 | Anderson et al. |
| 2014/0171901 | A1 | 6/2014 | Langsdorf et al. |
| 2015/0041498 | A1 | 2/2015 | Kakiuchi et al. |
| 2015/0051487 | A1 | 2/2015 | Uber et al. |
| 2015/0057613 | A1 | 2/2015 | Clemente et al. |
| 2015/0064036 | A1 | 3/2015 | Eberhard |
| 2015/0137017 | A1 | 5/2015 | Ambrosina et al. |
| 2015/0202386 | A1 | 7/2015 | Brady et al. |
| 2015/0290389 | A1 | 10/2015 | Nessel |
| 2015/0297825 | A1 | 10/2015 | Focht et al. |
| 2016/0008549 | A1 | 1/2016 | Plumptre et al. |
| 2016/0025544 | A1 | 1/2016 | Kamen |
| 2016/0055842 | A1 | 2/2016 | Defranks et al. |
| 2016/0082242 | A1 | 3/2016 | Burton et al. |
| 2016/0129190 | A1 | 5/2016 | Haitsuka |
| 2016/0193423 | A1 | 7/2016 | Bilton |
| 2016/0213851 | A1 | 7/2016 | Weibel et al. |
| 2017/0021096 | A1 | 1/2017 | Cole et al. |
| 2017/0021137 | A1 | 1/2017 | Cole |
| 2017/0100541 | A1 | 4/2017 | Constantineau et al. |
| 2017/0216516 | A1 | 8/2017 | Dale |
| 2017/0239415 | A1 | 8/2017 | Hwang et al. |
| 2017/0290975 | A1 | 10/2017 | Barmaimon et al. |
| 2018/0021521 | A1 | 1/2018 | Sanchez |
| 2018/0185579 | A1 | 7/2018 | Joseph et al. |
| 2018/0313346 | A1 | 11/2018 | Oakes |
| 2019/0192782 | A1 | 6/2019 | Pedersen et al. |
| 2019/0365993 | A1 | 12/2019 | Staub et al. |
| 2020/0009315 | A1 | 1/2020 | Brouet et al. |
| 2020/0345931 | A1 | 11/2020 | Gray et al. |
| 2022/0218895 | A1* | 7/2022 | Yang ................ A61M 5/14236 |
| 2022/0362465 | A1* | 11/2022 | Cardinali ............... F04B 49/06 |

FOREIGN PATENT DOCUMENTS

| | | | |
|---|---|---|---|
| CN | 102498292 | B | 7/2015 |
| CN | 204972511 | U | 1/2016 |
| CN | 105764543 | B | 7/2016 |
| CN | 206175149 | U | 5/2017 |
| CN | 107096091 | A | 8/2017 |
| CN | 108472441 | A | 8/2018 |
| DE | 4200595 | A1 | 7/1993 |
| DE | 19723648 | C1 | 8/1998 |
| DE | 102005040344 | A1 | 3/2007 |
| EP | 0454331 | A1 | 10/1991 |
| EP | 0789146 | A1 | 8/1997 |
| EP | 867196 | A2 | 9/1998 |
| EP | 1065378 | A2 | 1/2001 |
| EP | 1177802 | A1 | 2/2002 |
| EP | 1403519 | A1 | 3/2004 |
| EP | 2397181 | A1 | 12/2011 |
| EP | 2468338 | A1 | 6/2012 |
| EP | 2703024 | A1 | 3/2014 |
| EP | 1874390 | B1 | 10/2014 |
| EP | 2830499 | A1 | 2/2015 |
| FR | 2096275 | A5 | 2/1972 |
| FR | 2455269 | A1 | 11/1980 |
| FR | 2507637 | A1 | 12/1982 |
| FR | 2731475 | A1 | 9/1996 |
| GB | 357139 | A | 9/1931 |
| GB | 810488 | A | 3/1959 |
| GB | 875034 | A | 8/1961 |
| GB | 1204836 | A | 9/1970 |
| GB | 2008806 | A | 6/1979 |
| GB | 2077367 | A | 12/1981 |
| GB | 2456681 | A | 7/2009 |
| GB | 2549750 | A | 11/2017 |
| IL | 46017 | A | 11/1977 |
| JP | 06063133 | A | 3/1994 |
| JP | H06296690 | A | 10/1994 |
| JP | H08238324 | A | 9/1996 |
| JP | 2004247271 | A | 9/2004 |
| JP | 2004274719 | A | 9/2004 |
| JP | 2005188355 | A | 7/2005 |
| JP | 2006159228 | A | 6/2006 |
| JP | 6098988 | B2 | 9/2006 |
| JP | 2006249130 | A | 9/2006 |
| JP | 2009514580 | A | 4/2009 |
| JP | 2017513577 | A | 6/2017 |
| NL | 1019126 | C1 | 4/2003 |
| WO | 8101658 | A1 | 6/1981 |
| WO | 8606796 | A1 | 11/1986 |
| WO | 9320864 | A1 | 10/1993 |
| WO | 9415660 | A1 | 7/1994 |
| WO | 9855073 | A1 | 12/1998 |
| WO | 9856293 | A1 | 12/1998 |
| WO | 9910040 | A1 | 3/1999 |
| WO | 9910049 | A1 | 3/1999 |
| WO | 9962576 | A1 | 12/1999 |
| WO | 0029047 | A1 | 5/2000 |
| WO | 0178812 | A1 | 10/2001 |
| WO | 0220073 | A2 | 3/2002 |
| WO | 0226282 | A2 | 4/2002 |
| WO | 2002076535 | A1 | 4/2002 |
| WO | 2003097133 | A1 | 4/2002 |
| WO | 02068823 | A1 | 9/2002 |
| WO | 2004032994 | A2 | 4/2004 |
| WO | 2004056412 | A2 | 7/2004 |
| WO | 2004110526 | A1 | 12/2004 |
| WO | 2007066152 | A2 | 6/2007 |
| WO | 2008133702 | A1 | 11/2008 |
| WO | 2009039203 | A2 | 3/2009 |
| WO | 2009141005 | A1 | 11/2009 |
| WO | 2010022069 | A2 | 2/2010 |

(56) References Cited

FOREIGN PATENT DOCUMENTS

| | | | |
|---|---|---|---|
| WO | 2010077279 | A1 | 7/2010 |
| WO | 2010139793 | A1 | 12/2010 |
| WO | 2011010198 | A2 | 1/2011 |
| WO | 2011031458 | A1 | 3/2011 |
| WO | 2011069935 | A2 | 6/2011 |
| WO | 2011075042 | A1 | 6/2011 |
| WO | 2011133823 | A1 | 10/2011 |
| WO | 2012073032 | A1 | 6/2012 |
| WO | 2013050535 | A2 | 4/2013 |
| WO | 2013137893 | A1 | 9/2013 |
| WO | 2013149186 | A1 | 10/2013 |
| WO | 2014029416 | A1 | 2/2014 |
| WO | 2014149357 | A1 | 9/2014 |
| WO | 2014179774 | A1 | 11/2014 |
| WO | 2015032772 | A1 | 3/2015 |
| WO | 2015048791 | A1 | 4/2015 |
| WO | 2015081337 | A2 | 6/2015 |
| WO | 2015117854 | A1 | 8/2015 |
| WO | 2015167201 | A1 | 11/2015 |
| WO | 2015177082 | A1 | 11/2015 |
| WO | 2017148855 | A1 | 9/2017 |
| WO | 2017187177 | A1 | 11/2017 |
| WO | 2021016452 | A1 | 1/2021 |
| WO | 2022116602 | A1 | 6/2022 |

OTHER PUBLICATIONS

Lind et al. "Linear Motion Miniature Actuators." Paper presented at the 2nd Tampere International Conference on Machine Automation, Tampere, Finland (Sep. 1998).

Author Unknown "The Animas R-1000 Insulin Pump—Animas Corporation intends to exit the insulin pump businessand discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/.

Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.

Vaughan, M.E., "The Design, Fabrication, and Modeling of a Piezoelectric Linear Motor." Master's thesis, Virginia Polytechnic Institute and State University, VA. (2001).

Galante et al., "Design, Modeling, and Performance of a High Force Piezoelectric Inchworm Motor," Journal of Intelligent Material Systems and Structures, vol. 10, 962-972 (1999).

International Search Report and Written Opinion for International Application No. PCT/US2017/055054, mailed on Jan. 25, 2018, 13 pages.

International Search Report and Written Opinion for International Application No. PCT/US2018/045155, mailed on Oct. 15, 2018, 15 pages.

International Preliminary Report on Patentability for International Application No. PCT/US2017/034811 issued on Nov. 27, 2018, 10 pages.

International Preliminary Report on Patentability for International Patent Application No. PCT/US2017/046508, Feb. 12, 2019, 10 pages.

International Search Report and Written Opinion for International Application No. PCT/US2017/046508, mailed on Jan. 17, 2018, 14 pages.

International Search Report and Written Opinion for International Application No. PCT/US2017/046777, mailed on Dec. 13, 2017, 14 pages.

International Search Report and Written Opinion for International Application No. PCT/US2017/046737, mailed on Dec. 14, 2017, 11 pages.

International Search Report and Written Opinion for International Application No. PCT/US2017/034814, mailed on Oct. 11, 2017, 18 pages.

European Search Report and Written Opinion for the European Patent Application No. EP19177571, dated Oct. 30, 2019, 8 pages.

International Preliminary Report on Patentability for International Patent Application No. PCT/US2018/014351, dated Jul. 23, 2019, 7 pages.

International Preliminary Report on Patentability for International Patent Application No. PCT/US2017/046777, dated Feb. 19, 2019, 8 pages.

International Preliminary Report on Patentability for International Patent Application No. PCT/US2017/046737, dated Feb. 19, 2019, 8 pages.

International Preliminary Report on Patentability for International Patent Application No. PCT/US2017/055054, dated Apr. 9, 2019, 8 pages.

International Search Report and Written Opinion for Application No. PCT/US2017/034811, mailed Oct. 18, 2017, 15 pages.

EPO Search Report received in Application No. 13768938.6, dated Nov. 11, 2015, 8 pages.

International Search Report and Written Opinion for PCT Application No. PCT/US13/34674, mailed Aug. 6, 2013, 17 pages.

International Search Report and Written Opinion for International Application No. PCT/GB2007/004073, Jan. 31, 2008, 8 pages.

International Search Report and Written Opinion for International Patent Application No. PCT/US2019/063615, dated May 3, 2020, 17 pages.

International Preliminary Report on Patentability for International Patent Application No. PCT/US2018/045155, dated Feb. 14, 2020, 10 pages.

International Search Report and Written Opinion for International Patent Application No. PCT/US2019/035756, dated Jul. 31, 2019, 11 pages.

International Search Report and Written Opinion for PCT Application No. PCT/US2019/059854, mailed Aug. 26, 2020, 15 pages.

International Search Report and Written Opinion, Application No. PCT/US2022/016713, mailed Aug. 5, 2022, 19 pages.

International Search Report and Written Opinion for International Patent Application No. PCT/US2022/029012, mailed Aug. 19, 2022, 12 pages.

European Search Report and Written Opinion for European Patent Application No. EP20174878, dated Sep. 29, 2020, 8 pages.

Schott web-page image from Jul. 9, 2016, https://www.us.schott.com/pharmaceutical_packaging/english/products/cartridges.html.

International Search Report and Written Opinion for International Patent Application No. PCT/US2021/055581, dated Feb. 8, 2022, 19 pages.

International Search Report and Written Opinion for International Patent Application No. PCT/US2022/011356, dated Apr. 29, 2022, 19 pages.

International Search Report and Written Opinion for International Patent Application No. PCT/US2023/084564, dated Apr. 12, 2024, 12 pages.

* cited by examiner

DRUG DELIVERY DEVICE DRIVE SENSOR

CROSS-REFERENCE TO RELATED APPLICATION

This application claims priority to and the benefit of U.S. Provisional Application No. 63/476,076, filed Dec. 19, 2022, the entirety of which is incorporated herein by reference.

TECHNICAL FIELD

The disclosed embodiments generally relate to medication delivery. More particularly, the disclosed embodiments relate to techniques, processes, systems, and devices that use a dual wheel drive mechanism to deliver a medicament to a user.

BACKGROUND

In on-body drug delivery systems, power efficiency savings are strived for in a number of different areas with the hope of saving power to reduce the required size or quantity of a power supply system, such as a number of batteries. One area in which power savings would be beneficial is in the drive system of the pump mechanism of the on-body drug delivery system. For example, as explained in further detail below, substantial power savings may be achieved from minimizing the amount of time elements of the drive system have to energized. Drive systems that utilize shape memory alloy (SMA) wires would benefit by shortening the time the SMA wire is energized.

Present drive systems that utilize SMA wires and ratchet wheels may include tolerances to allow for overtravel of a non-driving drive arm to ensure that the drive arm has cleared a ratchet wheel tooth being driven by the drive arm.

Accordingly, there is a need for a more power efficient and compact drug delivery device drive mechanism for expelling a liquid drug from a reservoir.

SUMMARY

A drug delivery device drive mechanism is provided. The drug delivery device drive mechanism may include a first ratchet wheel, a second ratchet wheel, a first driving arm, a second driving arm, a first sensor contact, and a second sensor contact. In other embodiments, only a single ratchet wheel may be necessary. The first ratchet wheel may have a plurality of first drive teeth and the second ratchet wheel may have a plurality of second drive teeth. The second ratchet wheel and the first ratchet wheel may rotate about a common axis. The first driving arm is operable to engage a first drive tooth surface of the plurality of first drive teeth and rotate the first ratchet wheel in a first direction. The second driving arm may be operable to engage a second drive tooth surface of the plurality of second drive teeth and rotate the second ratchet wheel in the first direction. The first sensor contact may be operable to, in response to being contacted by the first driving arm, cause the second driving arm to stop pushing against the second ratchet wheel. The second sensor contact may be operable to, in response to being contacted by the second driving arm, cause the first driving arm to stop pushing against the first ratchet wheel.

Also disclosed is a drug delivery device drive system that includes control circuitry, a first ratchet wheel, a second ratchet wheel, a first driving arm, and a second driving arm. The first ratchet wheel may have a plurality of first ratchet wheel gear teeth and the second ratchet wheel may have a plurality of second ratchet wheel gear teeth. The first ratchet wheel and the second ratchet wheel may rotate in unison about a common axis. The first driving arm is operable to contact a respective gear tooth of the plurality of first ratchet wheel gear teeth. The second driving arm is operable to contact a respective gear tooth of the plurality of second ratchet wheel gear teeth. The control circuitry alternates between causing the first driving arm to contact the respective gear tooth of the plurality of first ratchet wheel gear teeth and causing the second driving arm to contact the respective gear tooth of the plurality of gear teeth of the first ratchet wheel gear teeth.

In another aspect, another drug delivery device drive system is provided that includes control circuitry, a drive mechanism, a first ratchet wheel, a second ratchet wheel, a first driving arm, a first sensor contact arm, and a second sensor contact arm. The drive mechanism is coupled to the control circuitry. The first ratchet wheel may have a plurality of first ratchet wheel gear teeth and the second ratchet wheel may have a plurality of second ratchet wheel gear teeth. The first ratchet wheel and the second ratchet wheel rotate in unison about a common axis. The first driving arm is coupled to the drive mechanism and operable to contact a respective gear tooth of the plurality of first ratchet wheel gear teeth and the first sensor contact arm is coupled to the drive mechanism and the control circuitry. The second driving arm is coupled to the drive mechanism and operable to contact a respective gear tooth of the plurality of second ratchet wheel gear teeth and the second sensor contact arm is coupled to the drive mechanism and the control circuitry. The first driving arm and the first sensor contact arm are in contact with one another, and the drive mechanism is operable to push the first driving arm and the first sensor contact arm against a surface of a respective first ratchet wheel gear tooth until the first sensor contact arm no longer contacts the first driving arm.

In yet a further aspect, a drug delivery system that includes an actuator, a first ratchet wheel, a second ratchet wheel, a first sensor contact, and a second sensor contact. The actuator includes a pivot point, an actuation tab, a first drive arm and a second drive arm. The first ratchet wheel may be operable to be pushed by the first drive arm and the second ratchet wheel may be operable to be pushed by the second drive arm. The first sensor contact is operable to be contacted by the first drive arm; and the second sensor contact is operable to be contacted by the second drive arm. Contact by the first drive arm with the first sensor contact causes the actuator to apply force via the first drive arm to push the first ratchet wheel.

BRIEF DESCRIPTION OF THE DRAWINGS

In the drawings, like reference numbers generally refer to the same parts throughout the different views. In the following description, various embodiments of the present disclosure are described with reference to the following drawings, in which.

The drawings are not necessarily to scale. The drawings are merely representations, not intended to portray specific parameters of the disclosure. The drawings are intended to depict exemplary embodiments of the disclosure, and therefore are not to be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and techniques in accordance with the present disclosure will now be described more fully hereinafter with reference to the accompanying drawings, where one or more embodiments are shown. The systems, devices, and techniques may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and techniques disclosed herein provides one or more advantages over conventional systems, components, and methods.

In the disclosed drive system, the tolerances related to drive arm overtravel may be removed since the described drive system sensor arrangement waits for a tooth clearance signal that indicates the drive arm has cleared the drive tooth. This enables an energy savings on each ratchet pulse (or cycle) by properly timing the stroke of the drive arm. If the stroke is too long, extra energy is used and wasted. On the other hand, if the stroke is too short, the drive arm will not complete its stroke and the second ratchet drive arm may not be able to turn the ratchet wheel causing missed insulin delivery. With two driving arms turning respective ratchet wheels, an optimum stroke occurs at exactly the time/distance required for the inactive drive arm to fall off the previous ratchet wheel tooth, making the inactive drive arm ready to become the active drive arm and start a ratchet pulse or cycle. The foregoing advantages are realized by adding sensor contacts to a two drive arm drive mechanism configuration, which allows for detection of when the non-driving drive arm is ready to start a ratchet pulse or cycle.

Figure 1:
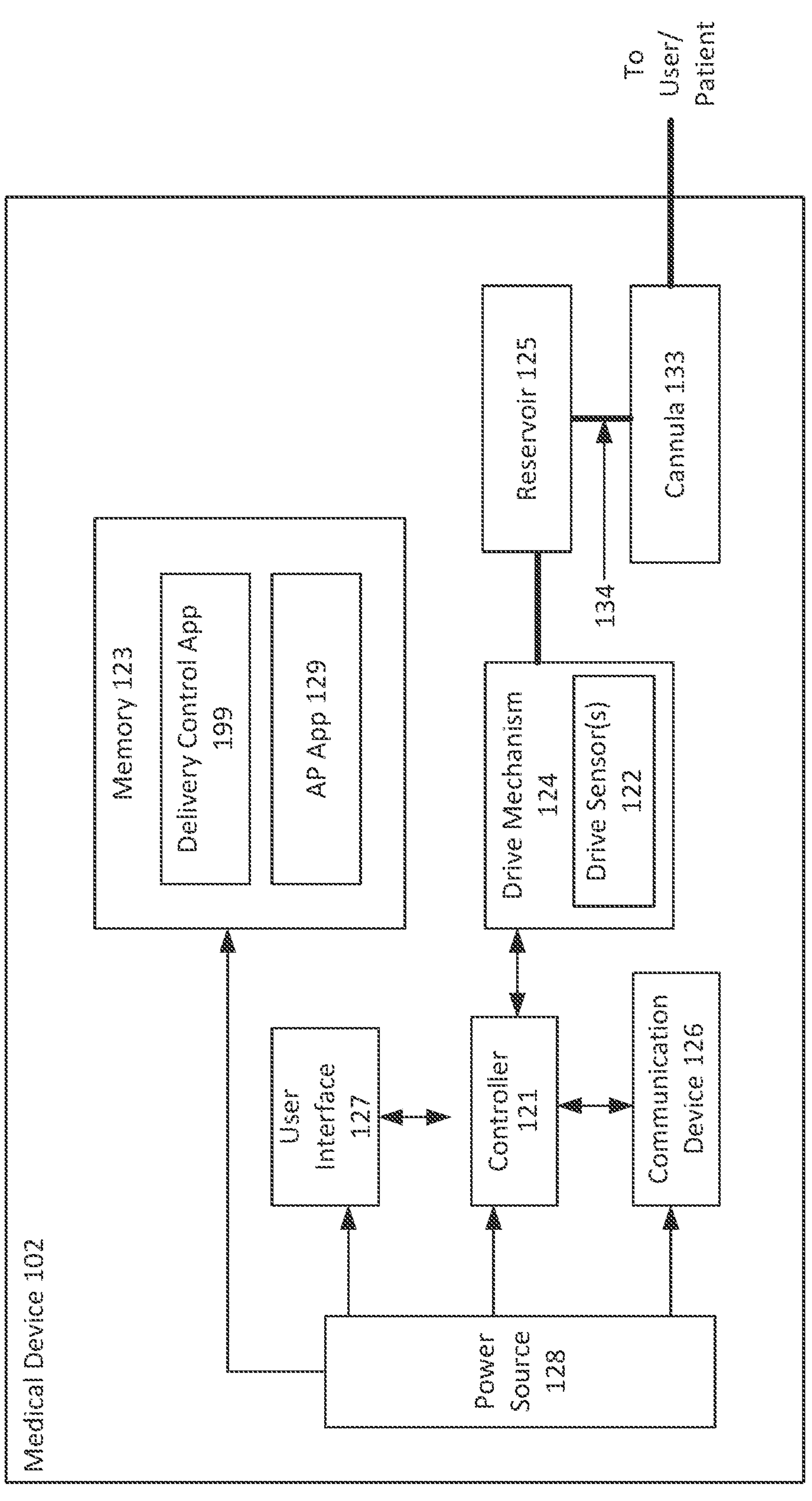
FIG. 1 illustrates a schematic diagram of a drug delivery system according to embodiments of the present disclosure.

FIG. 1 illustrates a simplified block diagram of an example drug delivery device. The drug delivery device 100 may include a controller 121, a memory 123, an AP application 129 and delivery control application 199 stored in the memory 123, a drive mechanism 124, a communication device 126, user interface 127, and a power source 128. The memory 123 may be operable to store programming code and applications including a delivery control application 199, the AP application 129 and data. The delivery control application 199 and the AP application 129 may optionally be stored on other devices.

The AP application 129 may be operable to perform various functions related to open loop operations, such as determination of a total daily setting for a drug or combination of drugs, such as a total daily insulin setting or the like. In an example, the AP application 129 configured to provide automatic delivery of insulin, via the delivery control application 199, based on an analyte sensor input, such as signals received from an analyte sensor, such as a continuous blood glucose monitor, or the like. The delivery control application 199 may, for example, be operable to interpret or apply signals provided by the AP application 129 to the drive mechanism 124 and/or the user interface 127.

The controller 121 may be coupled to the drive mechanism 124 and the memory 123. The controller 121 may include logic circuits, a clock, a counter or timer as well as other processing circuitry, and be operable to execute programming code and the applications stored in the memory 123 including the delivery control application 199. A communication device 126 may be communicatively coupled to the controller 121 and may be operable to wirelessly communicate with an external device, such as a personal diabetes management device, a smart device such as a smartphone and/or a smartwatch, or the like.

The drive mechanism 124 may be operable to deliver a drug, like insulin, at a fixed or variable rate. For example, an AP application or AID algorithm executing on a personal diabetes management device or a smart phone may determine or be informed that a user's total daily insulin (e.g., bolus and/or basal deliveries) is 48 units per 24 hours, which may translate to an exemplary physiological basal dosage rate of 1 unit per hour (48/24/2 (assuming a 1:1 basal/bolus ratio)) that may be determined according to a diabetes treatment plan. Of course, the drive mechanism 124 may be operable to deliver insulin at rates different from the example physiological dosage rate of 1 unit per hour. In an example, the system 100 may be attached to the body of a user, such as a patient or diabetic via, for example, by an adhesive, (e.g., directly attached to the skin of the user) and may deliver any therapeutic agent, including any drug or medicine, such as insulin, morphine, or the like, to the user. In an example, a surface of the system 100 may include an adhesive (not shown) to facilitate attachment to a user. The system 100 may, for example, be worn on a belt or in a pocket of the user and the liquid drug may be delivered to the user via tubing to an infusion site on the user.

In various examples, the system 100 may be an automatic, wearable drug delivery device. For example, the system 100 may include a reservoir 125 configured to hold a liquid drug (such as insulin), a needle and/or cannula 133 for delivering the drug into the body of the user (which may be done subcutaneously, intraperitoneally, or intravenously), and a drive mechanism 124, or other drive mechanism, for transferring the drug from the reservoir 125, through a needle or cannula 133, and into the user.

The drive mechanism 124 may be fluidly coupled to reservoir 125, and communicatively coupled to the medical device controller 121. The drive mechanism 124 may be coupled to the reservoir 125 and operable to output the liquid drug from the reservoir 125 via a fluid delivery path and out of the cannula 133. The drive mechanism 124 may have mechanical parameters and specifications, such as a pump resolution, that indicate mechanical capabilities of the drive mechanism. The drive mechanism 124 may also have electrical connections to control circuitry (not shown) that is operable to control operation of the drive mechanism 124. The pump resolution is a fixed amount of insulin the drive mechanism 124 delivers in a drive mechanism pulse, which is an actuation of the drive mechanism for a preset time period. Actuation may be when power from the power source 128 is applied to the control circuitry coupled to the drive mechanism 124 and the drive mechanism 124 operates to pump a fixed amount of insulin in a preset amount of time from the reservoir 125. Alternatively, the drive mechanism 124 may be substantially mechanical in structure and operation and utilize mechanical energy storage devices, such as springs or other biasing members to operate the drive mechanism 124. A drive sensor(s) 122 may be coupled to elements of the drive mechanism 124, such as ratchet wheels, or the like. The drive sensor(s) 122 may be a circuit that either has a high potential or ground potential that is monitored by the controller 121.

The cannula 133 of FIG. 1 may be coupled to the reservoir 125 via a fluid delivery path 134. The cannula 133 may be operable to output the liquid drug to a user when the cannula 133 is inserted in the user.

The system 100 may also include a power source 128, such as a battery, a supercapacitor, a piezoelectric device, or the like, that is operable to supply electrical power to the drive mechanism 124 and/or other components (such as the controller 121, memory 123, and the communication device 126) of the system 100.

The controller 121 may be implemented in hardware, software, or any combination thereof. In various examples, the controller 121 can be implemented as dedicated hardware (e.g., as an application specific integrated circuit (ASIC)). The controller 121 may be a constituent part of the system 200, can be implemented in software as a computational model, or can be implemented external to the system 100 (e.g., remotely). The controller 121 may be configured to communicate with one or more sensors (not shown).

A reservoir 125, may be included in a drug delivery device to store a liquid drug (e.g., insulin). For example, the reservoir 125 may be filled, or partially filled, with a liquid drug or a liquid drug solution. In one example, a liquid drug solution is a mixture of the liquid drug and added preservatives. The reservoir may store the liquid drug until all of the liquid drug has been dispensed (e.g., into a patient via a cannula). As such, the liquid drug (or solution) may remain in the reservoir for a period of time (e.g., 1 day, 3 days, 1 week, 2 weeks, etc.).

The medical device 102 may be a wearable drug delivery device that is worn on the body of the user. For example, an adhesive may couple the medical device 102 to the skin of a user's body. The medical device 102 may be a multi-part device. For example, the medical device 102 as a wearable drug delivery device may have a first part and a second part that couple or connect together. The first part and/or second part may fit into or slide into a tray or cradle that is adhered to the user's body, and the first part and/or second part may be removable from the tray. If using a first part and a second part, the first part may comprise reusable components (e.g., electronic circuitry, processor, memory, a drive mechanism, and potentially a rechargeable battery), and the second part may comprise disposable components (e.g., a reservoir, a needle and/or cannula, a disposable battery, and other portions or components that come into contact with the liquid drug or medicament). Moreover, the first part and the second part may contain their own housing or may combine together to form a single housing. The wearable drug delivery device 102 may be directly coupled to a user (e.g., directly attached to a body part and/or skin of the user via an adhesive, directly, via the tray, or the like). In an example, a surface of the wearable drug delivery device 102 or a tray into which the wearable drug delivery device 102 couples may include an adhesive to facilitate attachment to the skin of a user.

While the medical device 102 is described with reference to delivery of insulin and the use of an AID algorithm, the medical device 102 may be operable to implement a drug delivery regimen via a medication delivery algorithm using a number of different liquid or therapeutic drugs. A liquid drug may be or include any drug in liquid form capable of being administered by a drug delivery device via a subcutaneous cannula, including, for example, insulin, glucagon-like peptide-1 (GLP-1), pramlintide, glucagon, co-formulations of two or more of GLP-1, pramlintide, and insulin; as well as pain relief drugs, such as opioids or narcotics (e.g., morphine, or the like), methadone, arthritis drugs, hormones, such as estrogen and testosterone, blood pressure medicines, chemotherapy drugs, fertility drugs, or the like.

Figure 2A:
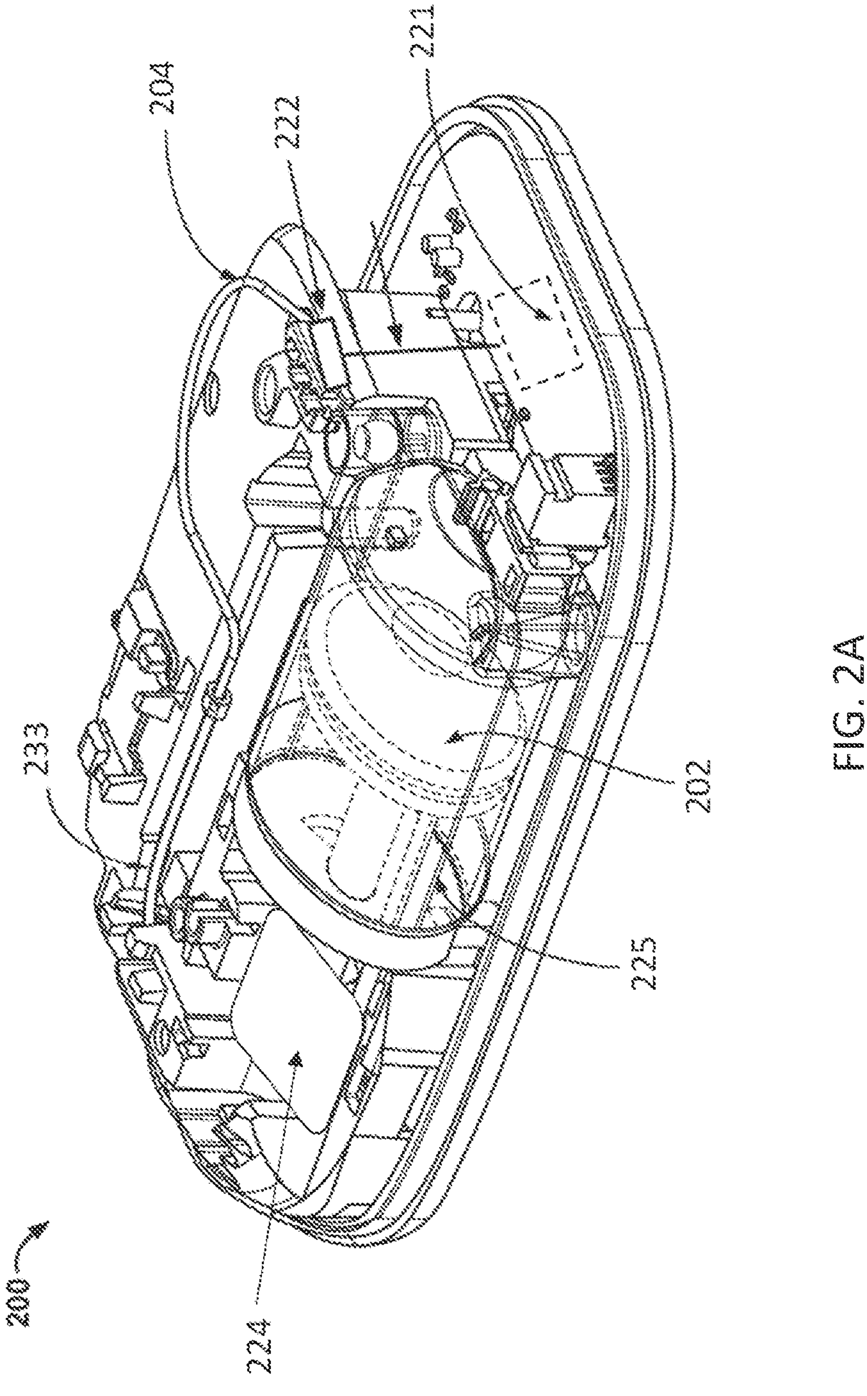
FIG. 2A illustrates a perspective view of a drug delivery system according to embodiments of the present disclosure.

As shown in FIG. 2A, the system 200 may include a plunger 202 positioned within the reservoir 225. An end portion or stem of the plunger 202 can extend outside of the reservoir 225. The drive mechanism 224 may, under control of the controller 221, be operable to cause the plunger 202 to expel the fluid, such as a liquid drug (not shown) from the reservoir 225 and into a fluid component 204 and cannula 233 by advancing into the reservoir 225. In various examples, a pressure sensor, such as that shown at 222, may be integrated anywhere along the overall fluid delivery path of the system 200, which includes the reservoir 225, the fluid delivery path component 204, and the cannula 233.

The controller 221 may be implemented in hardware, software, or any combination thereof. In various examples, the controller 221 can be implemented as dedicated hardware (e.g., as an application specific integrated circuit (ASIC)). The controller 221 may be a constituent part of the system 200, can be implemented in software as a computational model, or can be implemented external to the system 200 (e.g., remotely). The controller 221 may be configured to communicate with one or more sensors (e.g., sensor(s) 108 of FIG. 1).

As described above, a reservoir, such as 225, may be included in a drug delivery device to store a liquid drug (e.g., insulin). For example, the reservoir 225 may be filled, or partially filled, with a liquid drug or a liquid drug solution. In one example, a liquid drug solution is a mixture of the liquid drug and added preservatives. The reservoir may store the liquid drug until all of the liquid drug has been dispensed (e.g., into a patient via a cannula). As such, the liquid drug (or solution) may remain in the reservoir for a period of time (e.g., 1 day, 3 days, 1 week, 2 weeks, etc.).

Figure 2B:
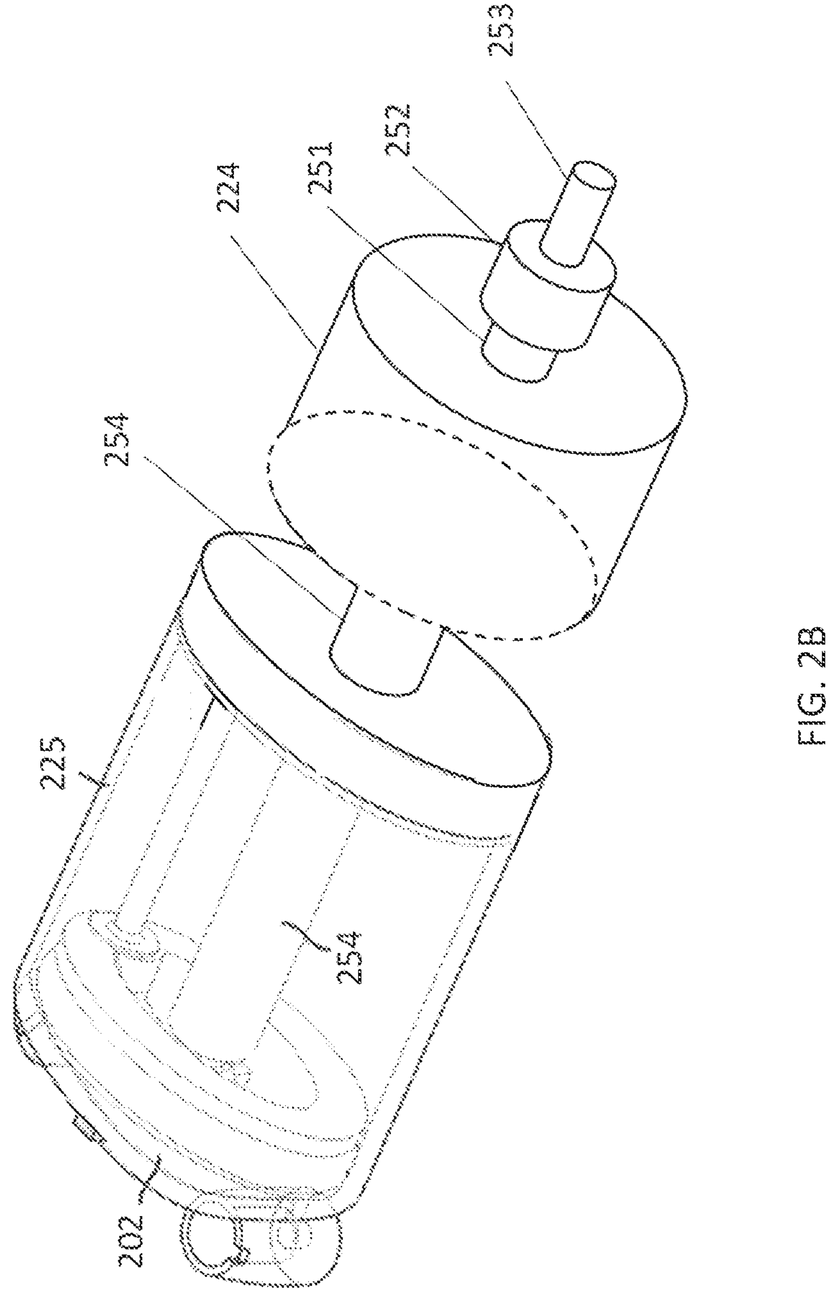
FIG. 2B illustrates a detailed perspective view of a portion of an example of a drug delivery system of FIG. 2A according to embodiments of the present disclosure.
Figure 2C:
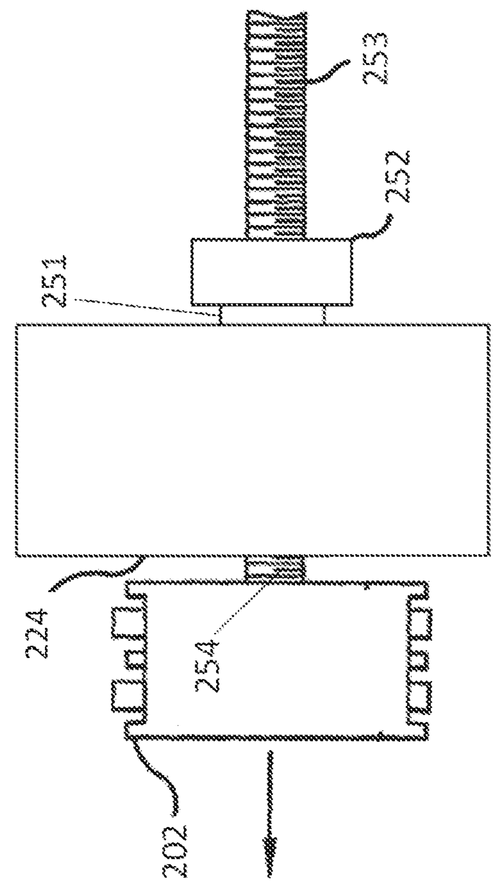
FIG. 2C illustrates a top view of an example of a drive mechanism of a drug delivery system of FIG. 2A according to embodiments of the present disclosure.

FIG. 2B illustrates an example of a reservoir coupled to the drive mechanism 224 in more detail than the view of FIG. 2A. Likewise, FIG. 2C illustrates a perspective view of the drive mechanism 250. As disclosed in later examples, the drive mechanism 224 (shown in more detail in later examples) may include co-axial ratchet wheels, drive arms, sensor contacts and an actuator. The co-axial ratchet wheels may be coupled to a plunger 202 via an elongated shaft 254. At a high level, the ratchet wheels of the drive mechanism 224 are engaged by the drive arms in response to a force applied by the actuator to incrementally advance the plunger 202 and the elongated shaft 254 into the reservoir 225. The elongated shaft 245 advances the plunger 202 to dispense the liquid drug out of the reservoir 225. In one example, a drive mechanism coupling 251 is operable to rotate a drive element 252 in response to forces applied to either the first ratchet wheel or the second ratchet wheel of the drive mechanism 224. The drive element 252 may include (or may be otherwise coupled to) a lead screw 253 that is coupled to the plunger 202 (e.g., via the elongated shaft 254). The drive element 252 is operable to rotate causing the lead screw 253 to advance the elongated shaft 254 and the plunger 202 within the reservoir 225 to expel the liquid drug from the reservoir 225.

In at least one embodiment, a drive mechanism is provided that may include a pair of co-axial ratchet wheels (i.e., first and second ratchet wheels) that are driven by a first driving arm and a second driving arm. In some examples, a sensor contact arrangement coupled to the first and second ratchet wheels allows the drive mechanism to be responsive to the travel of the respective ratchet arms in various implementations and configurations. In this context, a co-axial arrangement refers to an arrangement where the first and second rachet wheels rotate around the same axis or a common axis.

Figures 3A, 3B:
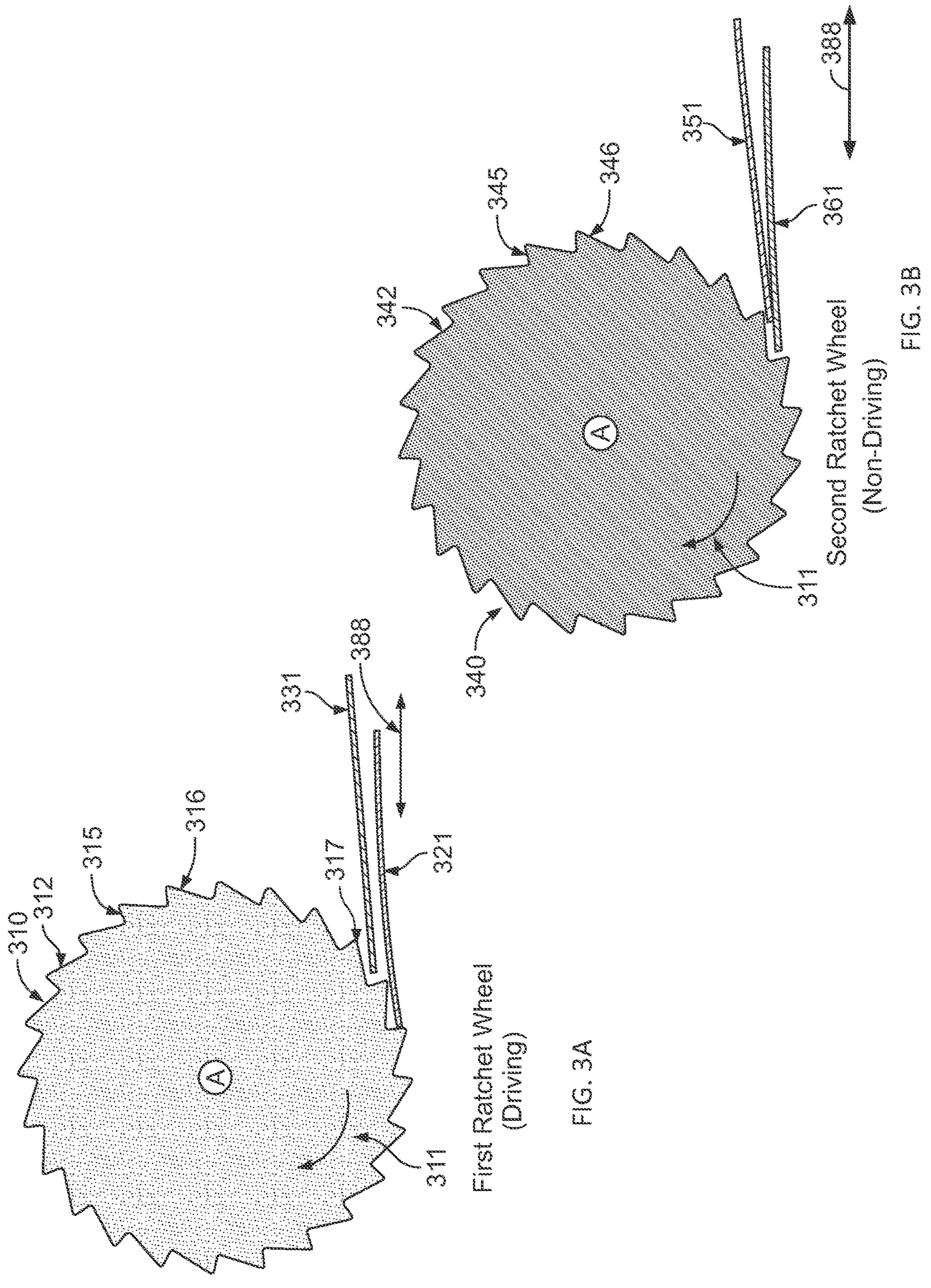
FIG. 3A illustrates an example of a first ratchet wheel and driving arms in a driving position that is a part of an example drive system according to embodiments of the present disclosure.
FIG. 3B illustrates an example of a second ratchet wheel in a resting position that is another part of the example drive system that utilizes ratchet wheels having respective drive arms and respective sensor contact according to embodiments of the present disclosure.

FIGS. 3A and 3B illustrate individual ratchet wheels of the disclosed subject matter that are operable to work individually, or in cooperation, to drive a drive element that causes delivery of a liquid drug. The following discussion covers an example in which the first ratchet driving wheel and the second ratchet wheel operate in cooperation, but for ease of illustration and discussion, the respective ratchet wheels are shown separately to better show the positions of the respective driving arms and sensor contacts.

Each ratchet wheel may be configured with a number of gear teeth. For example, a first ratchet wheel 310 may have a number of first drive teeth, such as drive tooth 312 shown in FIG. 3A. Each drive tooth 312 may have a drive tooth surface 315 and drive tooth face 316. FIG. 3B shows a second ratchet wheel 340 that may also have a number of second drive teeth, such as drive tooth 342. Each drive tooth 342 may have a drive tooth surface 345 and drive tooth face 346. The second ratchet wheel 340 and the first ratchet wheel 310 may rotate about a common axis A shown in FIG. 3A.

As such, by coupling at least one of the first ratchet wheel 310 of FIG. 3A or the second ratchet wheel 340, or both, to a pumping mechanism (e.g., drive mechanism 224), the incremental rotational motion of the ratchet wheels 310 and 340 can be used to actuate the pump and deliver a liquid drug to a patient. For example, a drive mechanism coupling may be operable to connect either the first ratchet wheel 310 or the second ratchet wheel 340 to a drive element (e.g., the drive mechanism 224 of FIG. 2C). The drive element may include a leadscrew (and/or a tube nut that may be threadedly engaged with the leadscrew) coupled to a plunger (e.g., the plunger 202 of FIG. 2B). In some examples, the size (e.g., diameter) of the ratchet wheels 310, 340 controls the dosage provided by the drive mechanism. For example, larger diameter ratchet wheels may enable the drive mechanism 300 to operate the drive mechanism with a higher dosage resolution (e.g., smaller dosage sizes).

FIG. 3A shows an example of a first ratchet wheel driving cycle. In FIG. 3A, a first driving arm 321 may be operable to engage a first drive tooth surface, such as 315, of one drive tooth of the number of first drive teeth and rotate the first ratchet wheel 310 in a first direction 311. At the end of the driving cycle, the first driving arm 321 is shown pushing against a drive tooth surface, such as 315, of the drive tooth and the first sensor contact 331 is positioned at a next drive tooth 317. As shown in FIG. 3B, while the first driving arm 321 is pushing against a drive tooth surface, the second ratchet wheel 340 may be in a non-driving (or resting) cycle. At the end of the non-driving or resting cycle, the second driving arm 361 is in contact with the second sensor contact 351 and not pushing against a drive tooth surface of a drive tooth of the second ratchet wheel 340. In FIG. 3B, the second driving arm 361 is shown ahead (e.g., farther to the left or offset from a tip of the second sensor contact 351) of the second sensor contact 351. Both the first driving arm 321 and the second driving arm 361 may bend slightly to provide a spring force that allows the first driving arm 321 and the second driving arm 361 to spring (or flex) up to make contact with the respective sensor contacts 331 and 351. A controller, such as controller 121 of FIG. 1, may enable the generation of a first tooth clearance signal, causing the first driving arm 321 to stop driving.

The second sensor contact 351 is operable to be contacted by the second driving arm 361. In this example, the contact by the second sensor contact 351 with the second driving arm 361 may indicate to the controller (not shown in FIGS. 3A and 3B) that (i) the second driving arm 361 is in position with respect to the gear tooth surface, or (ii) the first driving arm 321 has completed a full stroke of pushing against its corresponding drive tooth surface, or both (i) and (ii). As the first ratchet wheel 310 and the second ratchet wheel 340 rotate in response to the force applied by first driving arm 321, the second driving arm 361 may slide along its corresponding drive tooth face toward the second sensor contact 351 and a next drive tooth.

The intent of the illustrated example is allow the controller to determine as precisely as possible when the respective driving arm (i.e., either the first driving arm 321 or the second driving arm 351) drops off a drive tooth, so the controller is informed of when contact is made with the sensor contact and when the controller should optimally stop driving the first driving arm, because the second driving arm is ready to start driving, and vice versa.

Figures 3C, 3D:
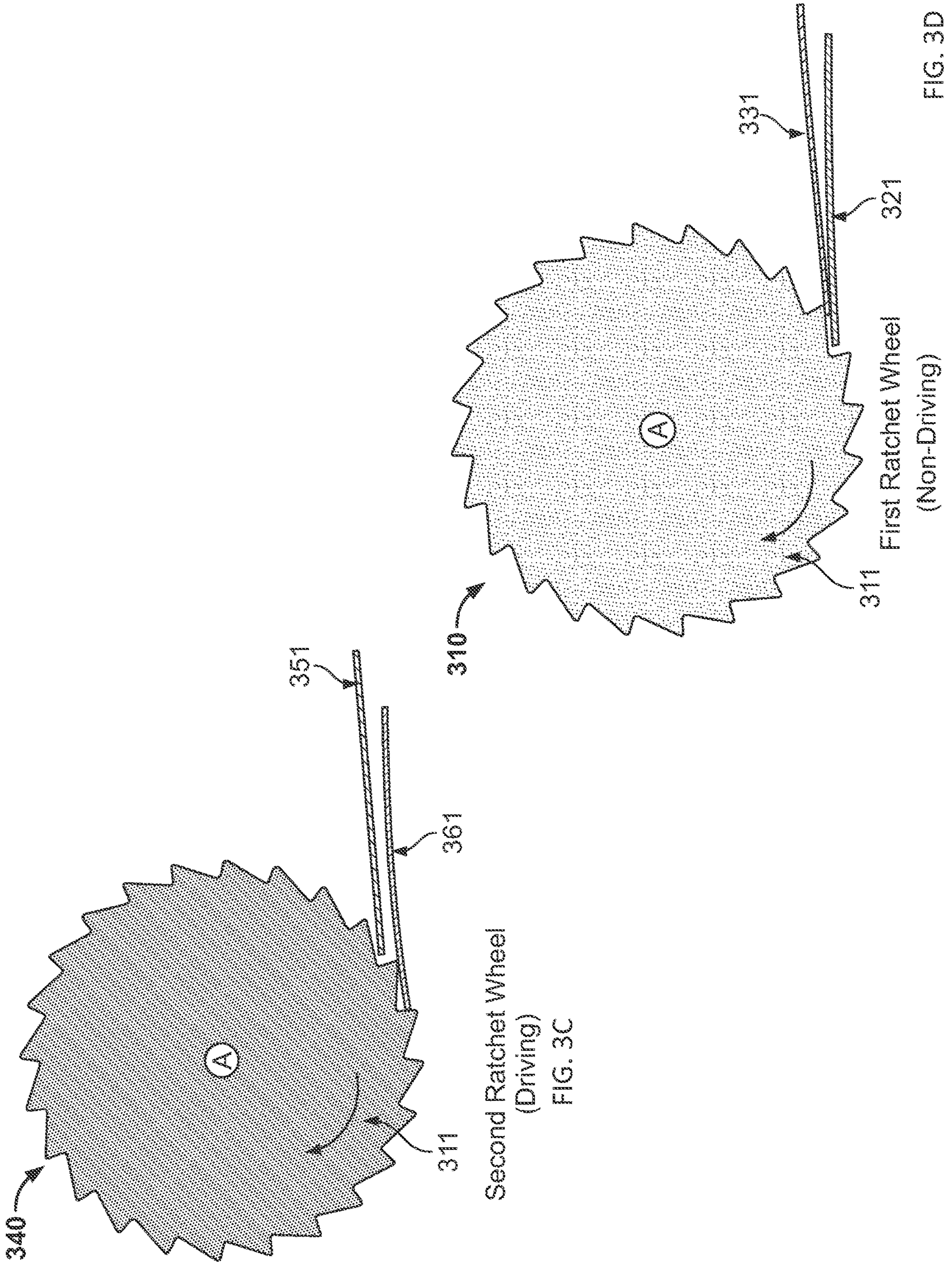
FIG. 3C shows the first ratchet wheel of the example of FIG. 3A in a resting position according to embodiments of the present disclosure.
FIG. 3D shows the second ratchet wheel of the example of FIG. 3B in a driving position according to embodiments of the present disclosure.

FIG. 3B shows the second ratchet wheel 340 in a reset position (e.g., resting or non-driving position), while FIG. 3C shows the second ratchet wheel 340 at the end of its driving cycle. Eventually, as the second driving arm 361 continues to rotate the second ratchet wheel 340 as shown in FIG. 3B, the second sensor contact 351 loses contact with the second driving arm 361 as the second sensor contact 351 falls to a next drive tooth of the second ratchet wheel 340 as shown in FIG. 3C. In the example, a second tooth clearance signal may be enabled (e.g., caused to be initiated) when the second sensor contact 351 loses contact with the second driving arm 361. For example, in response to the lost contact, a controller, such as controller 121 of FIG. 1, may enable the generation of a second tooth clearance signal that can, in conjunction with the first tooth clearance signal, be used to stop the driving of the second drive arm 361. The confirmation of the first and second tooth clearance signals alerts (i) that the first driving arm 321 is in position to begin pushing against a drive tooth face to begin rotating the first ratchet wheel and the second ratchet wheel in the direction 311 and (ii) that the second drive arm 361 and sensor contact 351 are positioned correctly for the next cycle. This near immediate response to the second driving arm being in position enables the controller to conserve the energy stored in the power source, i.e., power source 128 of FIG. 1.

Similarly, when the first driving arm 321 contacts the first sensor contact 331, the controller is operable to cause the second driving arm 361 to stop pushing against the second ratchet wheel 340 as shown in FIG. 3C and FIG. 3D. For example, the controller may be operable to enable a first tooth clearance signal when the first driving arm 321 contacts the first sensor contact 331. The first tooth clearance signal indicates that the second driving arm 361 is in position to apply a force against a next second drive tooth 342 of the number of second drive teeth. Note that the use of terminology such as "first tooth clearance signal" and "second tooth clearance signal" are not intended to indicate any temporal requirement of or limitation to the order of the respective tooth clearance signals. While one of the first or second driving arms is driving the respective ratchet wheel, the controller 121 is monitoring the driving sensor contact of the non-driving arm. The controller 121, in one example, may monitor the drive sensor(s) 122 for contact by a driving arm with a respective driving sensor contact. In some examples, the controller 121 may be monitoring for a driving arm to either make contact or lose contact with driving sensor contact the respective rachet wheel signal, e.g., the first tooth clearance signal or the second tooth clearance signal. This change in contact (i.e., making contact or losing contact) enables generation of a signal indicating the driving arm has fallen off the ratchet tooth and is ready to drive a ratchet wheel in a next pulse of the drive mechanism. A pulse of the drive mechanism may, for example, be considered the cycle of applying a force against a drive tooth surface and stopping the application of the force when a tooth clearance signal is generated.

In an example of a drive mechanism pulse, FIG. 3A shows the first driving arm 321 at the end of its drive stroke and in FIG. 3B, the second driving arm 361 is shown after it has fallen off a ratchet wheel gear tooth and contacted the second sensor contact 351. In the example of FIGS. 3A-3D, the two separate first sensor contact 331 and second sensor contact 351 may be fixed cantilever beams (i.e., are not moved left to by a drive mechanism), while the respective driving arms 321 and 361 are operable to move, via forces applied by a drive mechanism, linearly from right to left to drive the respective ratchet wheel/gear. In response to the forces applied by a drive mechanism, the respective ratchet wheel may be operable to rotate clockwise (i.e., in direction 311) while pivoting around its center (e.g., common axis A).

FIGS. 3C and 3D show a next cycle of the drive mechanism. In response to the first ratchet wheel 310 (that may be coupled to the second ratchet wheel 340 in an exemplary embodiment) being pushed in the direction 311 and the second ratchet wheel being offset by one-half of a drive tooth and also rotating, once the second drive arm 361 falls to the next drive tooth and contacts the second sensor contact 351, the controller can allow the second driving arm 361 to begin driving the second ratchet wheel 340 that causes the second ratchet wheel 340 to rotate in direction 311. While the second driving arm 361 is driving the second ratchet wheel, the first driving arm 321 is resting on or contacting a tooth surface 316, which indicates to a controller continue to drive the second driving arm 361 since the first driving arm 321 is not ready to be driven.

As shown in the examples of FIGS. 3A-3D, an improved drive system is provided by adding at least one extra cantilever arm in a drive mechanism. The two extra cantilever arms (i.e., sensor contacts) shown in the figures and interfacing the ratchet wheel can be non-driving on a ratchet tooth either before or after the driving arms. The sensor contacts may be part of individual circuits (described in more detail below with reference to FIGS. 4B and 4C) either open or closed when in contact with the driving arm depending upon the arrangement of the driving arms and sensor contacts.

For example, if the sensor contact is located before the non-driving arm, the circuit will be open and looking for a closed circuit to alert the driving arm to stop pushing. Since the driving arm is turning the wheel, the non-driving arm will eventually fall off the next tooth onto the sensor contact, closing the circuit. The motion of the arm falling off the tooth is the non-driving arm moving into a position to enable continued driving of the ratchet wheel(s).

Figure 4A:
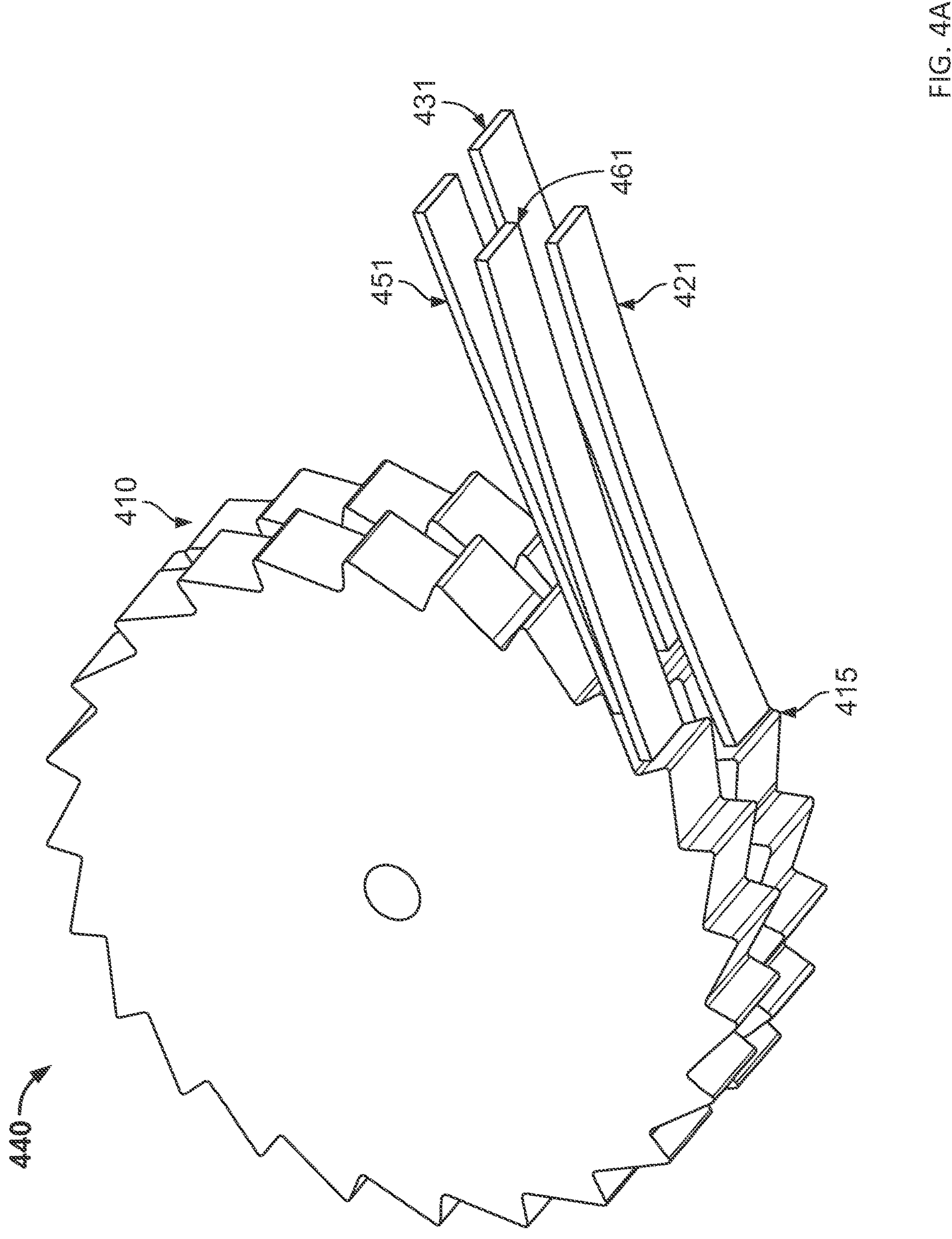
FIG. 4A illustrates a perspective view of a ratchet wheel configuration with respective drive arms and sensor contacts according to embodiments of the present disclosure.

FIG. 4A illustrates a further example configuration of the first and second ratchet wheels about a common axis. In FIG. 4A, the first ratchet wheel 410 and the second ratchet wheel 440 are arranged so that the respective drive teeth of each ratchet wheel are offset by approximately one-half of a drive tooth from one another. By being offset, the respective driving arms 421, 461, when driven are substantially certain to push the ratchet wheel a distance that enables the adjacent non-driving sensor contact to fall off the respective gear tooth surface of the adjacent ratchet wheel. In the example of FIG. 4A, the first driving arm 421 is driving the first ratchet wheel 410 by applying force to drive tooth surface 415. The second driving arm 461 just fell off the tooth face that it was resting upon, onto the second sensor contact 451 allowing the controller to stop driving the first driving arm 421.

Figure 4B:
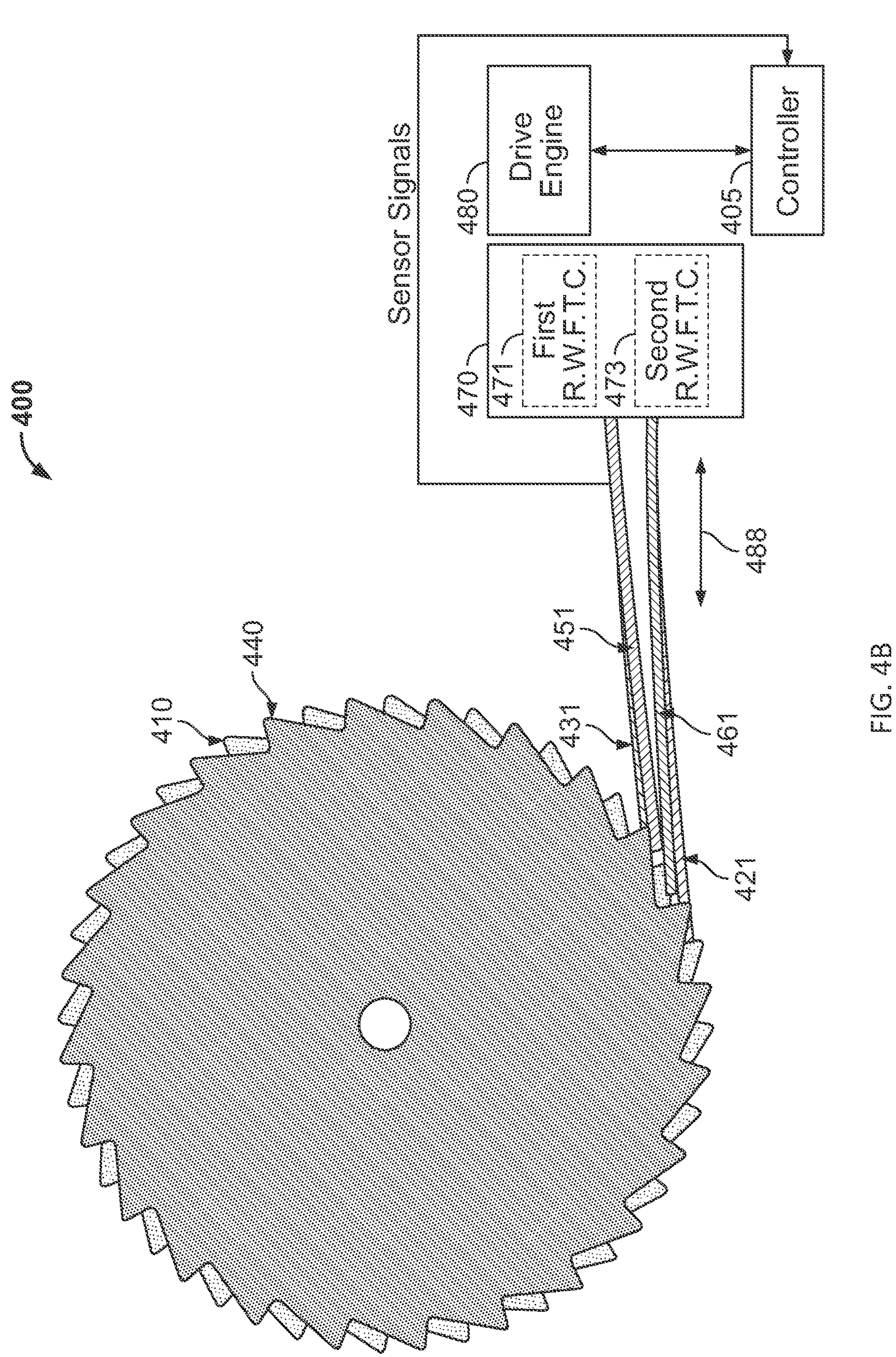
FIG. 4B illustrates an example drive mechanism system according to embodiments of the present disclosure.

Note that while the ratchet wheels are shown substantially in contact with one another in FIGS. 4A and 4B, it is not necessary that the ratchet wheels contact one another. It may be beneficial to describe more details of an example of a drive mechanism system incorporating the ratchet wheel configuration example of FIG. 4A.

FIG. 4B illustrates an example of a drive mechanism system. The drive mechanism system 400 may include a first ratchet wheel 410 and a second ratchet wheel 440, a first driving arm 421, a first sensor contact 431, a second driving arm 461, a second sensor contact 451, a ratchet force transfer coupling 470, a drive engine 480, and a controller 405. The ratchet wheel force transfer coupling 470 may be configured to apply a force to the respective first driving arm 421 and the second driving arm 461. The applied force by the ratchet wheel force transfer coupling 470 may configured to alternate between applying force to the first driving arm 421 and, subsequently, to the second driving arm 461.

In an example, the ratchet wheel force transfer coupling 470 may be configured to have two separate force transfer couplings, a first ratchet wheel force transfer coupling 471 and a second ratchet wheel force transfer coupling 473. The first ratchet wheel force transfer coupling 471 may be operable to apply a force to the first driving arm 421 and the second ratchet wheel force transfer coupling 473 may be operable to apply a force to the second driving arm 461. The sensor contacts 431 and 451 may be configured to be fixed cantilever beams that may be offset from respective driving arms 421, 461 so as to mitigate the possibility of creating a capacitive circuit between the respective drive arm and corresponding sensor contact (e.g., 461 and 451). In this example, the first ratchet wheel force transfer coupling 471 and the second ratchet wheel force transfer coupling 473 may be operable to alternate in the application of the force to the respective first driving arm 421 and the second driving arm 461 based on the making or losing of contact with the respective sensor contacts 431, 451 as described herein and with reference to FIGS. 3A-4A.

In a further example, in addition to monitoring only whether resting driving arm has lost contact with its respective sensing contact, the controller 405 may be operable to implement a two-step check. The controller 405 may make the two-step check by verifying that both the resting arm has contacted its respective sensing contact and the driving arm that is being driven has lost contact with its respective sensing contact.

The drive engine 480 may be mechanically coupled to the ratchet wheel force transfer coupling 470 or, respective individual ratchet wheel force transfer couplings 471 and 473, and may be any of a number of different mechanisms configurable to apply alternating force to the respective drive arms 421, 461. Examples of a drive engine mechanism may include a linear actuator, an electro-magnetic coil arrangement, a shape memory alloy, a biasing element, such as a spring or elastic member, a bent plastic member (that has a spring-like force), a combination of the foregoing mechanisms, or the like. The drive engine 480 may be electrically coupled to a controller 405 that is operable to actuate the drive engine 480 in response to sensor signals, such as those described with reference to the earlier examples.

The examples described with reference to FIGS. 3A-4B described a signaling example in which a controller monitored for a closed circuit between the respective drive arm and the respective sensor contact. However, it is also envisioned in an alternative example, that the controller is operable to monitor for an open circuit between the respective drive arm and the respective sensor contact. In the examples of FIGS. 3A-4B, the respective driving arms are shown on the outside (or on top) of the sensor contacts and, in operation, the driving arms fall onto their respective sensor contacts.

In the alternate example, the position of the sensor contacts and the drive arms is reversed. For example, if the sensor contact is located "above" the non-driving arm (which is opposite that shown in FIGS. 3A-3D), the circuit may be closed and looking for an open circuit to alert the driving arm to stop pushing. Since the driving arm is turning the wheel, the non-driving arm will eventually fall off the next tooth, opening the circuit. The motion of the arm falling off the tooth is the non-driving arm moving into a position that would enable it to continue driving the ratchet wheel. In this configuration, the driving arm is beneath the sensor contact and as the driving arm pushes against a respective ratchet wheel gear tooth surface, the other driving arm of the other ratchet wheel is not in contact with the other sensor contact until the other ratchet wheel travels far enough that the sensor contact falls off the ratchet wheel gear tooth that it was resting upon. In this configuration, the controller may monitor for multiple signals or a signal having a predetermined duration before starting to drive the other driving arm.

Figure 4C:
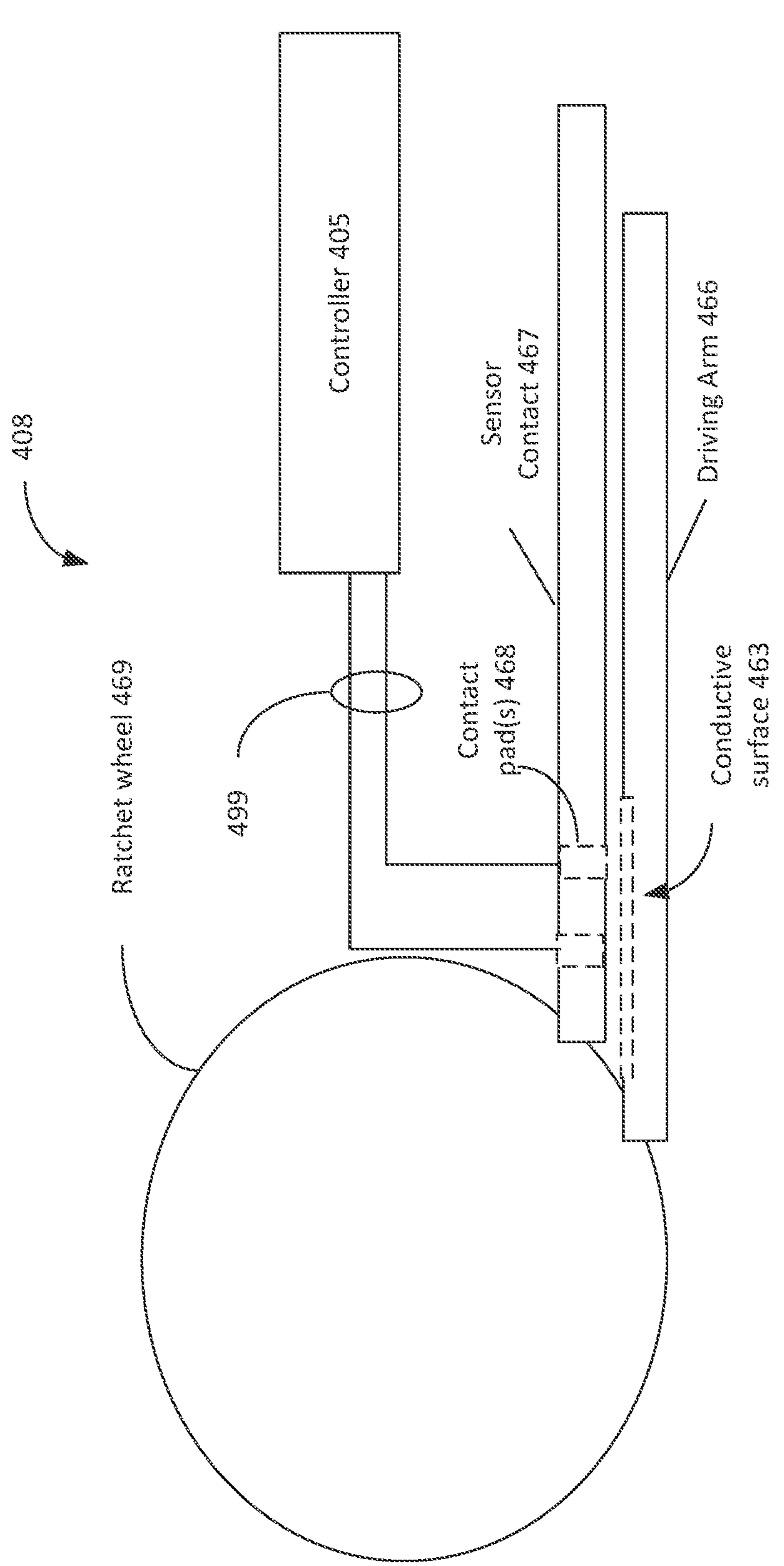
FIG. 4C illustrates an example sensor arrangement usable in the embodiments of the present disclosure.

FIG. 4C illustrates an example sensor configuration for a ratchet wheel in a system as shown in the example of FIG. 4B. The system 408 may include an example of ratchet 469, a controller 405, a driving arm 466 and a sensor contact 467. The sensor contact 467 may include one or more contacts, such as contact pad(s) 468. The contact pad(s) 468 may be connected to controller 405. The driving arm 466 may include a conductive surface 463. In an example, the contact pad(s) 468 on the sensor contact 467 may be embedded in a first surface of the sensor contact 467 facing the driving arm with vias that extend through the sensor contact 467 to a second surface where signal paths 499 couple the contact pad(s) 468 to the controller 405. A circuit between the two wires of the signal path 499 may be closed by the conductive surface 463 of the driving arm 466 establishing contact across both contact pad(s) 468, and the circuit is open when the conductive surface 463 does not establish contact across both contact pad(s) 468. The controller 405 may be configured to detect when the circuit is open or closed and take appropriate action, such as signaling a drive arm to stop rotating a ratchet wheel, or the like.

Figure 5A:
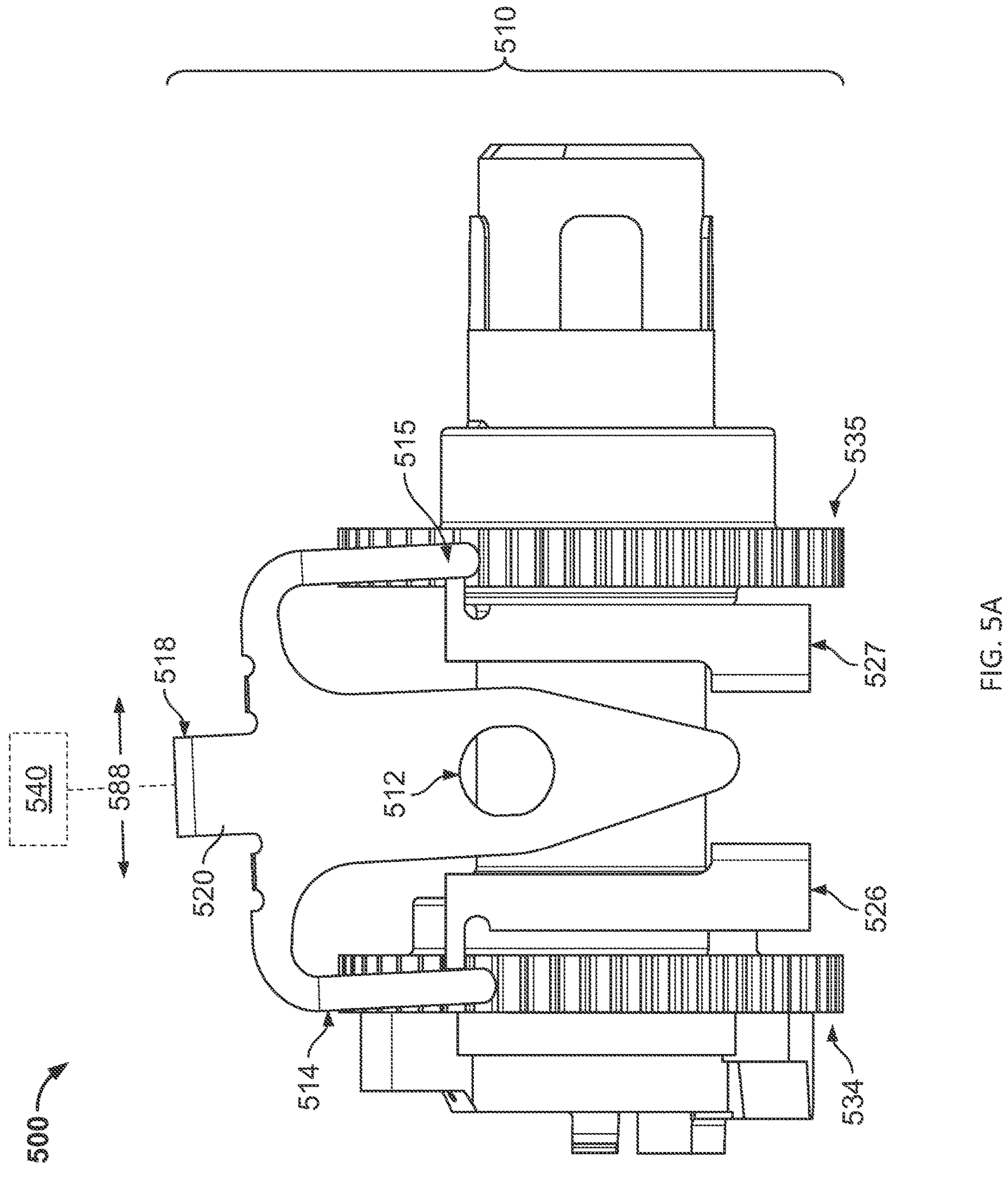
FIG. 5A illustrates a top view of an example drive mechanism of a liquid drug delivery device incorporating the sensor arrangement examples according to embodiments of the present disclosure.
Figure 5B:
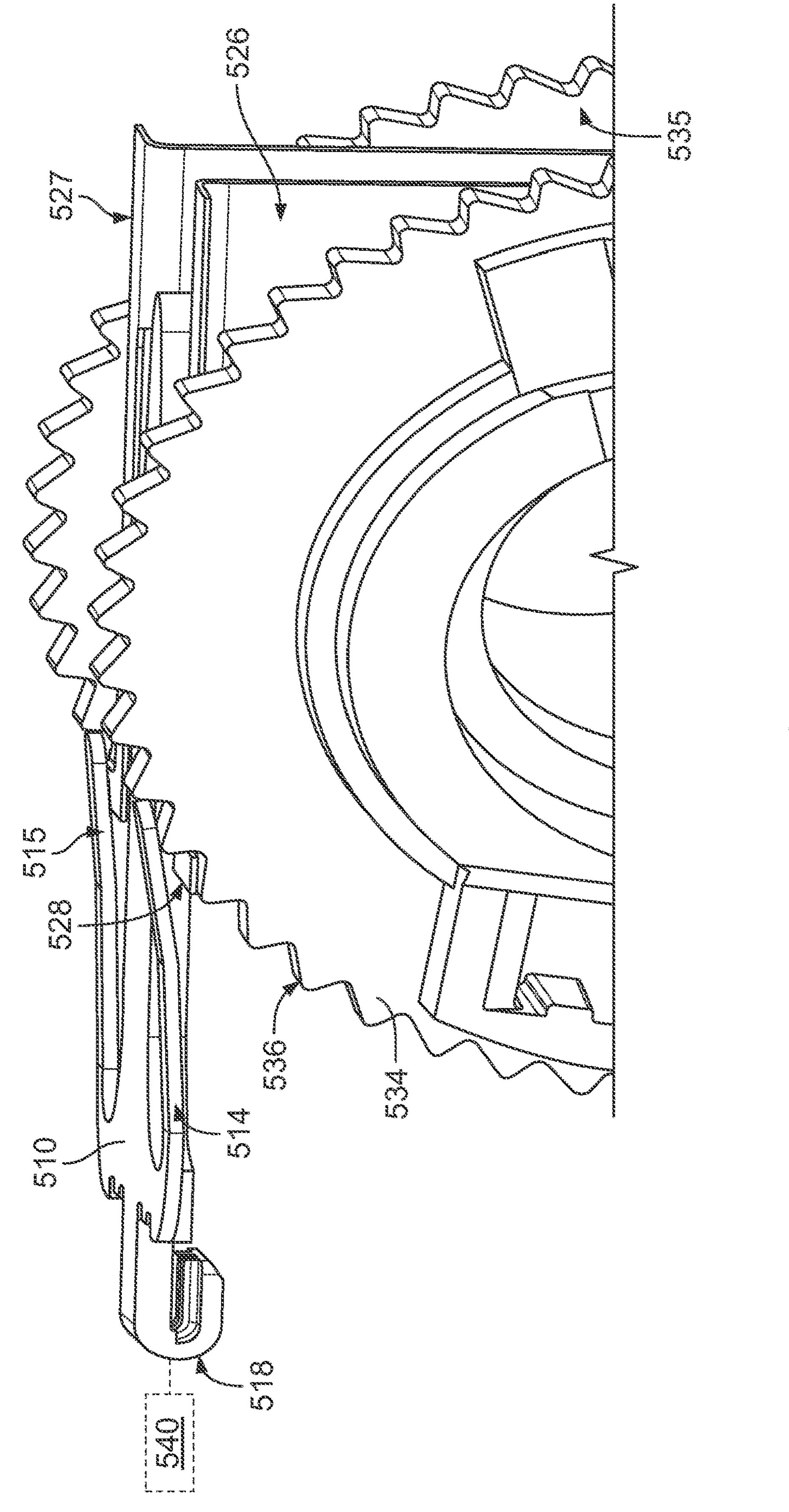
FIG. 5B illustrates a perspective view to the example drive mechanism of FIG. 5A.

Alternative configurations of the ratchet wheels are also envisioned, such as separating the ratchet wheels in an alternate drive mechanism system. FIGS. 5A and 5B provide an example of an alternate drive mechanism system. The drive mechanism 500 may include an actuator 540 and a drive mechanism 510. The drive mechanism 510 may include a first ratchet wheel 534, a second ratchet wheel 535, a drive member 520, drive sensor contact arms 526 and 527. The drive member 520 includes a first drive arm 514, a second drive arm 515, a pivot point 512 and an actuator coupling 518. The actuator 540 is configured to couple to the actuator coupling 518 and move the drive member 520 in the directions shown by arrow 588. The actuator 540 may be at least one shape memory alloy wire, an elastic structure, a spring, a yoke, or a combination of one or more of the shape memory alloy wire, the elastic structure, the spring, or the yoke. In the example, the actuator coupling 518 may be operable to engage the yoke of the actuator 540, be affixed to (e.g., via a crimp, an adhesive, Velcro, or a clamp) the shape memory alloy wire, the elastic structure, the spring or the like.

Similar to the examples of FIGS. 3A-4B, the first and second drive arms 514 and 515 are operable to alternately push against a drive tooth surface of the respective first ratchet wheel 534 and the second ratchet wheel 535. In this example, the first driving arm 514 and the first sensor contact arm 526 are configured to be substantially offset so only a portion of the first driving arm 514 and the first sensor contact arm 526 overlap. Similarly, the second driving arm 515 and the second sensor contact arm 527 are configured to be substantially offset so only a portion of the second driving arm 514 and the second sensor contact arm 527 overlap.

The first sensor contact arm 526 and the second sensor contact arm 527 are further coupled to a controller (shown in another example) as are a portion of the first driving arm 514 and a portion of the second driving arm 515 so as to either complete or open a circuit indicating a change from a driving cycle to a resting cycle or vice versa.

FIG. 5B shows an isometric view of the drive mechanism system 500. In this view, a portion 528 of the offset first sensor contact 526 is shown beneath the first drive arm 514 and resting on a face of a drive tooth, such as 536. In the example shown in FIGS. 5A and 5B, the first drive arm 514 is in a driving cycle and the second drive arm 515 is shown resting on a portion of the offset second sensor contact 527.

The example drive mechanism of FIGS. 5A and 5B are but one example of a drive mechanism operable to provide the functionality described herein.

Figure 6:
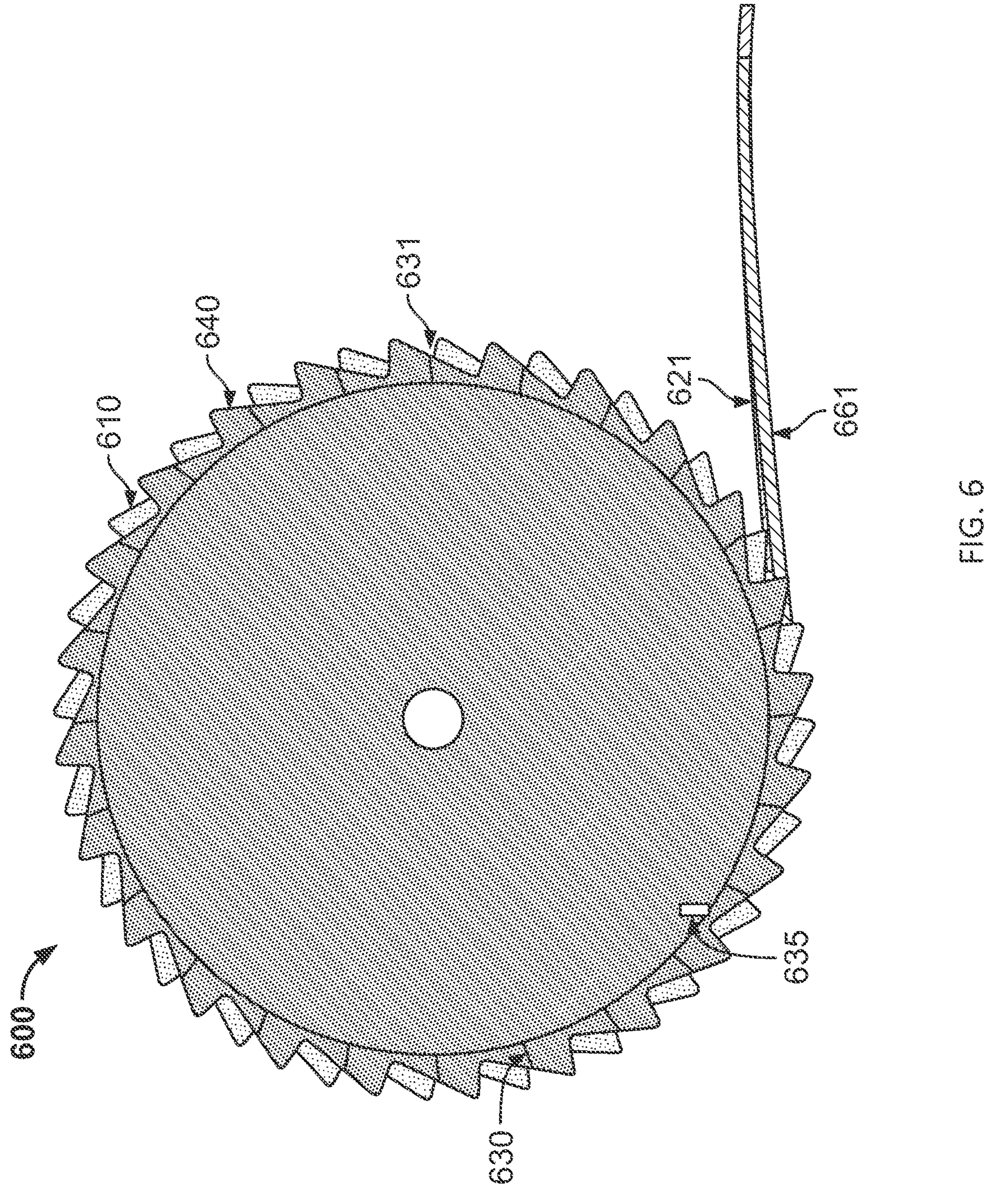
FIG. 6 illustrates an example operation of a drive mechanism of a liquid drug delivery device according to embodiments of the present disclosure.

FIG. 6 illustrates an example ratchet wheel configuration that utilizes an alternative sensor contact arrangement. In the ratchet wheel configuration 600 shown in FIG. 6, the first driving arm 621 and the second driving arm 661 are utilized to rotate the respective first ratchet wheel 610 and the second ratchet wheel 640. In this example the sensor contacts of the earlier examples are replaced by drive face contacts 631 that are coupled to a ring circuit 630 and a slip ring coupler 635. More particularly, the face of each tooth (either the entire face or only a portion of the face of each tooth) may have an electrical contact, such as 631, thereon such that a driving arm (e.g., 621 or 661) and the electrical contact on the tooth face form an electrical circuit when the driving arm is engaged with that particular tooth face. The slip ring coupler 635 may be electrically coupled to a controller that detects when the second drive arm 661 either makes contact with a drive tooth contact 631 and then loses contact with the drive tooth contact 631 as the second drive arm 661 begins to fall onto a next drive tooth or loses contact with a drive tooth contact 631 and then reestablishes contact with a subsequent drive tooth contact 632 on a next drive tooth (e.g., a follower tooth). For ease of illustration in FIG. 6, the ring circuit 630, the slip ring coupler 635 and drive tooth contacts 631 and 632 are only shown. However, the same arrangement of a ring circuit, slip ring coupler and drive tooth face contact may also (or alternatively) be present on the first ratchet wheel 610.

In an alternative embodiment similar to that shown in FIG. 6, only one ratchet wheel and one driving arm may be used. For example, with reference to the ratchet wheel 640 and driving arm 661 in FIG. 6, as the distal end of driving arm 661 advances ratchet wheel 640 to cause ratchet wheel 640 to rotate clockwise, the following (or "follower") tooth of rachet wheel 640 will eventually make contact with a proximal portion of driving arm 661. If each tooth face has an electrical contact, such as 631, formed thereon, and at least the proximal portion of driving arm 661 where the follower tooth makes contact with driving arm 661 also comprises an electrical contact (such as 632), then the follower tooth and the driving arm 661 will form an electrical circuit when driving arm 661 has advanced ratchet wheel 640 far enough such that the follower tooth of ratchet wheel 640 makes contact with the proximal portion of driving arm 661. When this electrical circuit is closed or completed, then the controller will know that driving arm 661 has advanced ratchet wheel 640 sufficiently far enough, and then driving arm can be pulled back (e.g., to the right in FIG. 6) a sufficient distance to cause driving arm 661 to fall off onto the next tooth (i.e., the follower tooth). The dimensions of the teeth will be known such that the controller knows how far back to pull driving arm 661 to cause it to fall off onto the next tooth. Then the process can repeat: the controller can cause driving mechanism to advance driving arm 661 to the left to force ratchet wheel 640 to rotate further clockwise until the next follower tooth makes contact with the proximal portion of driving arm 661.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

In particular, although the drug delivery device drive mechanism has been described above, and is defined in the enclosed claims, it should be understood that the drug delivery device drive mechanism according to the present disclosure can alternatively be defined in accordance with the following embodiments:

1. A drug delivery device drive system, comprising: control circuitry; a drive mechanism coupled to the control circuitry; a first ratchet wheel having a plurality of first ratchet wheel gear teeth; a second ratchet wheel having a plurality of second ratchet wheel gear teeth, wherein the first ratchet wheel and the second ratchet wheel rotate in unison about a common axis; a first driving arm coupled to the drive mechanism and operable to contact a respective gear tooth of the plurality of first ratchet wheel gear teeth; a first sensor contact arm coupled to the drive mechanism and the control circuitry; a second driving arm coupled to the drive mechanism and operable to contact a respective gear tooth of the plurality of second ratchet wheel gear teeth; and a second sensor contact arm coupled to the drive mechanism and the control circuitry, wherein, when the first driving arm and the first sensor contact arm are in contact with one another, the drive mechanism is operable to push the first driving arm against a surface of a respective first ratchet wheel gear tooth until the first sensor contact arm no longer contacts the first driving arm.
2. The drug delivery device drive system of embodiment 1, wherein the first ratchet wheel and the second ratchet wheel are operable to rotate in response to the pushing of the first driving arm and the first sensor contact against the surface of the respective first ratchet wheel gear tooth.
3. The drug delivery device drive system of embodiment 1 or 2, wherein the first sensor contact arm is configured to move to a next gear tooth surface of the plurality of first ratchet wheel gear teeth when the first sensor contact arm no longer contacts the first driving arm.
4. The drug delivery device drive system of one of embodiments 1 to 3, wherein, in response to the first sensor contact arm no longer contacting the first driving arm, and the second driving arm and the second sensor contact arm being in contact with one another, the control circuitry is operable to cause the drive mechanism to push the second driving arm and the second sensor contact arm against a surface of a respective second ratchet wheel gear tooth until the second sensor contact arm no longer contacts the second driving arm.

5. The drug delivery device drive system of one of embodiments 1 to 4, wherein the first ratchet wheel and the second ratchet wheel are operable to rotate in response to the pushing of the second driving arm and the second sensor contact against the surface of the respective second ratchet wheel gear tooth.

6. The drug delivery device drive system of one of embodiments 1 to 5, wherein the second sensor contact arm is configured to move to a next gear tooth surface of the plurality of second ratchet wheel gear teeth when the second sensor contact arm no longer contacts the second driving arm.

7. A drug delivery device drive system, comprising: an actuator including a pivot point, an actuation tab and a first drive arm; a first ratchet wheel operable to be pushed by the first drive arm; a first sensor contact operable to be contacted by the first drive arm; wherein contact by the first drive arm with the first sensor contact causes the actuator to apply force via the first drive arm to push the first ratchet wheel.

8. The drug delivery device drive system of embodiment 7, wherein, when the first drive arm is no longer in contact with the first sensor contact, the actuator stops applying force via the first drive arm to push the first ratchet wheel.

9. The drug delivery device drive system of embodiment 7 or 8, comprising: a second drive arm; a second ratchet wheel operable to be pushed by the second drive arm; and a second sensor contact operable to be contacted by the second drive arm, wherein contact by the second drive arm with the second sensor contact causes the actuator to apply force via the second drive arm to push the second ratchet wheel.

10. The drug delivery device drive system of embodiment 9, wherein, when the second drive arm is no longer in contact with the second sensor contact, the actuator stops applying force to the second drive arm and apply force via the second drive arm to the second ratchet wheel.

11. The drug delivery device drive system of one of embodiments 7 to 10, comprising: an actuator coupled to the actuation tab, wherein the drive actuator force transfer device is a shape memory alloy wire, an elastic structure, a spring, a yoke, or a combination of one or more of the shape memory alloy wire, the elastic structure, the spring, or the yoke.

12. The drug delivery device drive system of one of embodiments 9 to 11, wherein the first ratchet wheel and the second ratchet wheel rotate in a same direction around a common axis.

13. A drug delivery device drive system, comprising: a first ratchet wheel having a plurality of drive teeth, wherein each drive tooth of the plurality of drive teeth includes an electrical contact; a driving arm operable to contact the electrical contact of a first drive tooth of the plurality of drive teeth and rotate the first ratchet wheel in a first direction; and a controller operable to detect when the driving arm contacts the electrical contact of the first drive tooth.

14. The drug delivery device drive system of embodiment 13, wherein the controller is further operable to detect when the driving arm contacts an electrical contact of a second drive tooth of the plurality of drive teeth, subsequent to the first drive tooth.

15. The drug delivery device drive system of embodiment 13 or 14, wherein the controller is further operable to: in response to detecting that the driving arm contacted the electrical contact of the second drive tooth of the plurality of drive teeth, cause the driving arm to be moved away from a face of the first drive tooth, wherein the driving arm is positioned to engage a tooth face of the second drive tooth.

16. The drug delivery device drive system of one of embodiments 13 to 15, further comprising: a second ratchet wheel having a plurality of drive teeth, wherein each drive tooth of the plurality of drive teeth on the second ratchet wheel includes an electrical contact; a second driving arm operable to contact a first electrical contact of a first drive tooth of the plurality of drive teeth on the second ratchet wheel and rotate the second ratchet wheel in the first direction; and the controller is operable to detect when the second driving arm contacts a second electrical contact of the second drive tooth of the plurality of drive teeth on the second ratchet wheel.

17. The drug delivery device drive mechanism of one of embodiments 13 to 16, wherein the ratchet wheel and the other ratchet wheel rotate in a same direction around a common axis.

The invention claimed is:

1. A drug delivery device drive mechanism, comprising:

a first ratchet wheel having a plurality of first drive teeth;

a second ratchet wheel having a plurality of second drive teeth, wherein the second ratchet wheel and the first ratchet wheel rotate about a common axis;

a first driving arm operable to engage a first drive tooth surface of the plurality of first drive teeth and rotate the first ratchet wheel in a first direction;

a second driving arm operable to engage a first drive tooth surface of the plurality of first drive teeth and rotate the second ratchet wheel in the first direction;

a first sensor contact operable to, in response to being contacted by the first driving arm, cause the second driving arm to stop pushing against the second ratchet wheel; and a second sensor contact operable to, in response to being contacted by the second driving arm, cause the first driving arm to stop pushing against the first ratchet wheel.

2. The drug delivery device drive mechanism of claim 1, wherein the first sensor contact is further operable, when contacted by the first driving arm, to:

cause initiation of a first tooth clearance signal, wherein the first tooth clearance signal indicates that the first driving arm is in position to apply a force against a next first drive tooth of the plurality of first drive teeth.

3. The drug delivery device drive mechanism of claim 2, further comprising:

a first ratchet wheel force transfer coupling operable to apply a force to the first driving arm; and a second ratchet wheel force transfer coupling operable to apply a force to the second driving arm, wherein the first ratchet wheel force transfer coupling and the second ratchet wheel force transfer coupling alternate in the application of the force applied by each to the respective first driving arm and the second driving arm based in part on the generated first tooth clearance signal.

4. The drug delivery device drive mechanism of claim 1, wherein:

the first sensor contact is further operable to:

cause initiation of a first tooth clearance signal when contacted by the first driving arm, and the second sensor contact is further operable to:

cause initiation of a second tooth clearance signal when contacted by the second driving arm, wherein the first tooth clearance signal indicates that the first driving arm is in position to apply a force against a next first drive tooth of the plurality of first drive teeth and the second tooth clearance signal indicates that the second driving arm is in position to apply a force against a next second drive tooth of the plurality of second drive teeth.

5. A drug delivery device drive system, comprising:

control circuitry;

a first ratchet wheel having a plurality of first ratchet wheel gear teeth;

a second ratchet wheel having a plurality of second ratchet wheel gear teeth, wherein the first ratchet wheel and the second ratchet wheel rotate in unison about a common axis;

a first driving arm operable to contact a respective gear tooth of the plurality of first ratchet wheel gear teeth; and a second driving arm operable to contact a respective gear tooth of the plurality of second ratchet wheel gear teeth, wherein the control circuitry alternates between causing the first driving arm to contact the respective gear tooth of the plurality of first ratchet wheel gear teeth and causing the second driving arm to contact the respective gear tooth of the plurality of gear teeth of the first ratchet wheel gear teeth.

6. The drug delivery device drive system of claim 5, further comprising:

a first sensor contact arm coupled to the control circuitry; and a second sensor contact arm coupled to the control circuitry, wherein the first sensor contact arm enables input of a signal to the control circuitry in response to the first sensor contact arm being contacted by the first driving arm, and the second sensor contact arm enables input of another signal to the control circuitry in response to the second sensor contact arm being contacted by the second driving arm.

7. The drug delivery device drive system of claim 5, wherein:

the control circuitry switches to causing the second driving arm to contact the respective gear tooth of the plurality of gear teeth of the second ratchet wheel gear teeth in response to the first driving arm contacting the first sensor contact.

8. The drug delivery device drive system of claim 5, wherein:

the control circuitry switches to causing the first driving arm to contact the respective gear tooth of the plurality of first ratchet wheel gear teeth in response to the second driving arm contacting the second sensor contact.

9. The drug delivery device drive system of claim 5, wherein the first driving arm and the first sensor contact arm are configured to be substantially offset so only a portion of the first driving arm and the first sensor contact arm overlap.

10. The drug delivery device drive system of claim 5, wherein the second driving arm and the second sensor contact arm are configured to be substantially offset so only a portion of the second driving arm and the second sensor contact arm overlap.

11. The drug delivery device drive mechanism of claim 5, further comprising:

a first ratchet wheel force transfer coupling operable to apply a force to the first driving arm; and a second ratchet wheel force transfer coupling operable to apply a force to the second driving arm, wherein the first ratchet wheel force transfer coupling and the second ratchet wheel force transfer coupling alternate in the application of the force applied by each to the respective first driving arm and the second driving arm based in part on the generated first tooth clearance signal.

12. The drug delivery device drive mechanism of claim 5, further comprising:

a first ratchet wheel force transfer coupling operable to apply a force to the first driving arm; and a second ratchet wheel force transfer coupling operable to apply a force to the second driving arm, wherein the first ratchet wheel force transfer coupling and the second ratchet wheel force transfer coupling alternate in the application of the force applied by each to the respective first driving arm and the second driving arm based in part on the generated first tooth clearance signal.

13. A drug delivery device drive system, comprising:

control circuitry;

a drive mechanism coupled to the control circuitry;

a first ratchet wheel having a plurality of first ratchet wheel gear teeth;

a second ratchet wheel having a plurality of second ratchet wheel gear teeth, wherein the first ratchet wheel and the second ratchet wheel rotate in unison about a common axis;

a first driving arm coupled to the drive mechanism and operable to contact a respective gear tooth of the plurality of first ratchet wheel gear teeth;

a first sensor contact arm coupled to the drive mechanism and the control circuitry;

a second driving arm coupled to the drive mechanism and operable to contact a respective gear tooth of the plurality of second ratchet wheel gear teeth; and a second sensor contact arm coupled to the drive mechanism and the control circuitry, wherein the first sensor driving arm and the first sensor contact arm are in contact with one another, and the drive mechanism is operable to push the first driving arm and the first sensor contact arm against a surface of a respective first ratchet wheel gear tooth until the first sensor contact arm no longer contacts the first sensor driving arm.

14. The drug delivery device drive system of claim 13, wherein the first ratchet wheel and the second ratchet wheel are operable to rotate in response to the pushing of the first driving arm and the first sensor contact against the surface of the respective first ratchet wheel gear tooth.

15. The drug delivery device drive system of claim 13, wherein the first sensor contact arm is configured to:

move to a next gear tooth surface of the plurality of first ratchet wheel gear teeth when the first sensor contact arm no longer contacts the first sensor driving arm.

16. The drug delivery device drive system of claim 13, wherein, in response to the first sensor contact arm no longer contacting the first sensor driving arm, and the second sensor driving arm and the second sensor contact arm being in contact with one another, the control circuitry is operable to:

cause the drive mechanism to push the second driving arm and the second sensor contact arm against a surface of a respective second ratchet wheel gear tooth until the second sensor contact arm no longer contacts the second sensor driving arm.

17. The drug delivery device drive system of claim 16, wherein the first ratchet wheel and the second ratchet wheel are operable to rotate in response to the pushing of the second driving arm and the second sensor contact against the surface of the respective second ratchet wheel gear tooth.

18. The drug delivery device drive system of claim 16, wherein the second sensor contact arm is configured to:

move to a next gear tooth surface of the plurality of second ratchet wheel gear teeth when the second sensor contact arm no longer contacts the second sensor driving arm.

* * * * *